US005851781A

United States Patent [19]
Adamczyk et al.

[11] Patent Number: 5,851,781
[45] Date of Patent: Dec. 22, 1998

[54] REAGENTS AND METHODS FOR THE DETECTION AND QUANTIFICATION OF TESTOSTERONE IN FLUID SAMPLES

[75] Inventors: Maciej Adamczyk, Gurnee; Yon-Yih Chen, Mundelein, both of Ill.; John A. Walling, Charles City, Iowa; Bryan D. James, Chicago; Sharon G. Artrip, Elmhurst, both of Ill.

[73] Assignee: Abbott Laboratories, Abbott Park, Ill.

[21] Appl. No.: 432,439

[22] Filed: Apr. 28, 1995

Related U.S. Application Data

[62] Division of Ser. No. 102,083, Aug. 3, 1993, Pat. No. 5,491,071.

[51] Int. Cl.[6] .................................................. G01N 33/53
[52] U.S. Cl. .................. 435/7.9; 435/7.92; 435/7.93; 435/7.94; 435/7.95; 435/7.5; 435/962; 435/968; 424/1.45; 436/517; 436/518; 436/543; 436/544; 436/545; 436/546; 436/548; 436/817; 436/822
[58] Field of Search .................... 435/7.9, 7.92–7.93, 435/25, 26, 7.5, 172.2, 962, 968; 436/517, 518, 543–546, 548, 817, 822; 424/1.45; 530/388.1, 388.24, 388.9, 389.1, 389.2, 807

[56] References Cited

U.S. PATENT DOCUMENTS

| 3,907,842 | 9/1975 | Jones et al. | 530/363 |
| 4,031,117 | 6/1977 | Rao | 260/397.1 |
| 4,085,202 | 4/1978 | Rao | 436/542 |
| 4,150,105 | 4/1979 | Gross | 424/1 |
| 4,197,286 | 4/1980 | Rao | 424/1 |
| 4,279,992 | 7/1981 | Boguslaski et al. | 435/7.72 |
| 4,342,739 | 8/1982 | Kakimi et al. | 424/1 |
| 4,345,096 | 8/1982 | Bernstein et al. | 562/465 |
| 4,474,893 | 10/1984 | Reading | 436/547 |
| 4,510,251 | 4/1985 | Kirkemo et al. | 436/536 |
| 4,676,980 | 6/1987 | Segal et al. | 424/85 |
| 4,816,567 | 3/1989 | Cabilly et al. | 530/387 |
| 4,975,420 | 12/1990 | Silversides et al. | 514/15 |
| 5,002,883 | 3/1991 | Bieniarz et al. | 435/176 |
| 5,180,828 | 1/1993 | Ghazarossian et al. | 546/37 |
| 5,491,071 | 2/1996 | Adamczyk et al. | 435/25 |

FOREIGN PATENT DOCUMENTS

WO9320060 10/1993 WIPO ................................. 530/391.5

OTHER PUBLICATIONS

Bauminger et al., "Steroids as Haptens Optimal Design of Antigens for the Formation of Antibodies to Steroid Hormones," Journal of Steroid Biochemistry, 5 (1974): 739–747.

Jones et al, "The Use of 6α– and 6–β– carboxymethyl testosterone–bovine serum albumin conjugates in radioimmunoassay for testosterone," Steroids, 25 (1975) 23–32.

W. Eechaute et al., "The Conversion of Testosterone to 7α–Hydroxy–Testosterone by Incubated Rat Testes", Steroids, vol. 24:6, Dec. 1974, pp. 753–759.

R. Condom et al., "Preparation of Steroid–Antigens through Positions of the Steroid not Bearing Functional Groups", Steroids, vol. 23:4, Apr. 1974, pp. 483–498.

(List continued on next page.)

Primary Examiner—Carol A. Spiegel
Attorney, Agent, or Firm—David L. Weinstein

[57] ABSTRACT

The present invention discloses novel immunogens, antibodies prepared from such immunogens, and labeled reagents useful in immunoassays for the detection and quantification of testosterone in a test sample. Also disclosed are immunoassays using these reagents and methods for synthesizing these reagents. The immunoassays are preferably microparticle enzyme immunoassays (MEIAs) and fluorescence polarization immunoassays (FPIAs). Further disclosed are novel starting materials for making the above novel immunogens and labeled reagents. Methods for making the novel immunogens and labeled reagents from the novel starting materials are also disclosed.

21 Claims, 13 Drawing Sheets

OTHER PUBLICATIONS

M. Kocór et al., "Steroids. Part XLI. Michael Addition of Diethyl Malonate to Steroidal 3–Keto–1,4,6–Trienes", *Polish Journal of Chemistry*, vol. 53, 149, 1979, pp. 149–155.

J.F. Sabot et al., "Determination of Plasma Testosterone by Mass Fragmentography using (3.4–$^{13}$C) Testosterone as an Internal Standard", *Journal of Chromatography*, vol. 339 (1985) pp. 233–242.

Y. Shinohara et al., "Pharmacokinetic Studies of Testosterone Propionate Using Gas Chromatography/Mass Spectrometry/Selected Ion Monitoring", *Biomedical and Environmental Mass Spectrometry*, Vo. 16 (1988) pp. 241–244.

T. Furuta et al., "Simultaneous Measurements of Endogenous and Deutrium–labelled Tracer Variants of Androstenedione and testosterone by Capillary Gas Chromatography Mass Spectrometry", *Journal of Chromatography*, vol. 525 (1990) pp. 15–23.

S. Fukushima et al., "Simultaneous determination of Testosterone and Androstadienone (sex attractant) in human plasma by gas chromatography–mass spectrometry with high–resolution selected–ion monitoring", *Journal of Chromatography*, vol. 565 (1991) pp. 35–44.

S.A. Wudy et al., "Androgen metabolism assessment by routine gas chromatography/mass spectrometry profiling of plasma steroids: part 1, unconjugated steroids", *Steroids*, vol. 57 (1992), pp. 319–324.

L. Siekmann, "Determination of Steroid Hormones by the Use of Isotope Dilution–Mass Spectrometry: A Definitive Method in Clinical Chemistry", *Journal of steroid Biochemistry*, vol. 11 (1979), pp. 117–123.

G. Moneti et al., "Determination of Testosterone and its tissue metabolites (DHT and 3α–DIOL) in Human Plasma and Prostatic tissue by Isoptopic Dilution Mass Spectrometry", *Journal of Steroid Biochem*, vol. 27 (1897), p. 53–59.

P. Vingler et al., "Direct quatitative digital autoradiography–thin–layer chromatography 3α,3β– and 5α– reduced and 17β dehydrogenated androgens derived from testosterone metabolism", *Journal of Chromatography*, vol. 571 (1991) pp. 73–86.

A. Syropoulos et al., "Flow–injection chemiluminometric analysis of some steroids by their sensitizing effect on the bromate–sulphite reaction", *Analytica Chimica Acta*, vol. 239 (1990), pp. 195–202.

T.V. Stabler et al., "Chemiluminescence Immunoassay of Aldosterone in Serum", *Clinical Chemistry*, vol. 37 (1991), pp. 1988–1989.

Y. Suzuki et al., "Automated Direct Assay System for the Measurement of Sex Steroid Hormones in Serum using High–Performance Liquid Chromatography", *Journal of Chromatography*, vol. 426(1988), pp. 33–40.

F.U. Erkoc et al., "High–Performance Liquid Chromatographic Analysis of Steroid Hormones", *Journal of Chromatographic Science*, vol. 27 (1989), pp. 86–90.

H. Ueshiba et al., "Serum Profiles of Steroid Hormones in Patients with Cushing's Syndrome Determined by a New HPLC/RIA Method", *Clinical Chemistry*, vol. 37(1991), pp. 1329–1333.

H. Hosoda et al., "Sensitivity and Specificity in Enzyme Immunoassay of Testosterone", *Chemical Pharm. Bull.*, vol. 28(1980), pp. 3035–3040.

G.J. Marcus et al., "A Simple Enzyme–linked Immunosorbent Assay for Testosterone", *Steroids*, vol. 46(1985), pp. 975–986.

E. Ali et al., "Sandwich immunoassay of small molecules I. Investigation with testosterone as model hapten", *Journal of Immunological Methods*, vol. 147(1992), pp. 173–179.

J. Sengupta et al., "Sandwich immunoassay of small molecules, II. Effects of heterology and development of a highly sensitive and specific enzyme immunoassay for testosterone", *Journal of Immunological Methods*, vol. 147(1992), pp. 181–188.

T.K. Dhar et al., "Direct microlitre plate enzyme immunoassay of testosterone in unextracted serum", *Journal of Immunological Methods*, vol. 147(1992), pp. 167–172.

M.J. Rassaie et al., "A highly specific heterologous enzyme–linked immunosorbent assay for measuring testosterone in plasma using antibody–coated immunoassay plates or polypropylene tubes", *Steroids*, vol. 57(1992), pp. 288–294.

P.N. Rao et al., "Synthesis of New Steroid Haptens for Radioimmunoassay–Part V. 19–0–Carboxymethyl Ether Derivative of Testosterone. A Highly Specific Antiserum for Immunoassay of Testosterone from both Male and Female Plasma without Chromatography", *Journal of Steroid biochemistry*, vol. 9(1978), pp. 539–545.

M.J. Rassaie et al., "Influence of different combinations of antibodies and penicillinase–labeled testosterone derivatives on sensitivity and specificity of immunoassays", *Steroids*, vol. 57(1992), pp. 112–118.

H. Hosoda et al., "Preparation and Antigenic Properties of Testosterone–4–Bovine serum Albumin Conjugates", *Journal of Steroid Biochemistry*, vol. 10 (1979), pp. 513–517.

S.Z. Cekan, "On the Assessment of Validity of Steroid Radioimmunoassays", *Journal of Steroid Biochemistry*, vol. 11(1979), pp. 1629–1634.

T.W. Greene et al., *Protective Groups in Organic Synthesis*, 2nd Ed., John Wiley & Sons, Inc. New York, 1991, pp. v, ix and x.

Wekerle et al., "Striated muscle fibres differentiate in monolayer cultures of adult thymus reticulum", *Nature*, vol. 256 (1975), pp. 493–494.

G. Kohler et al., "Continuous cultures of fused cells secreting antibody of predefined specificity," *Nature*, vol. 256 (1975), pp. 495–497.

F. Kohen et al., "Non–radioisotopic Homogeneous Steroid Immunoassays," Journal of Steroid Biochemistry 11(1A):161–163, 166–7 (Jul. 1979) [No Text on pp. 164 & 165].

Chemical Abstract 92(17):147048, Yeda Research and Development Co. Ltd, "1α–Carboxyethylthio steroids and conjugates thereof with proteins," Apr. 28, 1980.

REAGENTS AND METHODS FOR THE DETECTION AND QUANTIFICATION OF TESTOSTERONE IN FLUID SAMPLES

This is a division of U.S. patent application Ser. No. 08/102,083 filed Aug. 3, 1993, now U.S. Pat. No. 5,491,071.

FIELD OF THE INVENTION

The present invention discloses novel immunogens, antibodies prepared from such immunogens, and labeled reagents useful in immunoassays for the detection and quantification of testosterone in a test sample. Also disclosed are immunoassays using these reagents and methods for synthesizing these reagents. The immunoassays are preferably microparticle enzyme immunoassays (MEIAs) and fluorescence polarization immunoassays (FPIAs). Further disclosed are novel starting materials for making the above novel immunogens and labeled reagents. Methods for making the novel immunogens and labeled reagents from the novel starting materials are also disclosed.

BACKGROUND OF THE INVENTION

Androgens are compounds which stimulate secondary sex characteristics and produce male secondary sex characteristics. The androgen 17 beta-Hydroxyandrost-4-en-3-one, commonly called testosterone, is synthesized in the interstitial (Leydig) cells of the testis in males. The synthesis of testosterone in the Leydig cells during adulthood is mainly controlled by the levels of pituitary luteinising hormone (LH). In females, there are three sources of testosterone biosynthesis. The adrenal glands and the ovaries secrete small quantities of testosterone, and the peripheral metabolism of androstenedione accounts for 50–60% of the daily testosterone production in normal females.

Testosterone exists in two forms in the blood stream: approximately 99% of the testosterone is bound to plasma proteins and the remainder is unbound. At least three serum proteins bind testosterone. Each protein binds testosterone with differing affinities. At physiological concentrations, the hormone is largely bound to a low capacity, high affinity beta-globulin, designated sex hormone binding globulin (SHBG). A smaller fraction is bound to albumin and to cortisol-binding globulin. The structural formula of testosterone and its numbering system is represented below:

STRUCTURAL FORMULA OF TESTOSTERONE

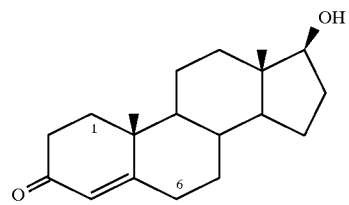

Testosterone is metabolized primarily in the liver. Enzymes have been identified in the skin and the reticuloendothelial system which are capable of metabolizing testosterone. Two major metabolic pathways of testosterone have been identified. In the 17-ketonic pathway, the 17 beta-hydroxy group is oxidized to a ketone. This results in the formation of the weak androgen, androstenedione. The pathway forms intermediate metabolites which have little biological activity. The second pathway, the 17-hydroxy route, involves changes initially in the A ring. In this pathway, the 17 beta-hydroxy group is not altered. This is important because the 17 beta-hydroxy group is required for the potency of androgenic steroids and their intermediate metabolites. Therefore, this metabolic pathway produces intermediate metabolites with considerable androgenic activity.

Clinical Utility

Testosterone measurements are useful in the evaluation of hypogonadal states. Common causes of decreased testosterone in males include: hypogonadism, orchidectomy, estrogen therapy, Klinefelter's syndrome, hypopituitarism, testicular feminization and hepatic cirrhosis.

In females, testosterone levels are normally found to be much lower than those encountered in the normal male. Common causes of increased serum testosterone levels in females include polycystic ovaries (Stein-Leventhal syndrome), ovarian tumors, adrenal tumors and adrenal hyperplasia. Virilization in women is associated with the administration of androgens and endogenous overproduction of testosterone.

Current Testosterone Assays

There are several methods available for the quantification of testosterone in serum. The techniques used to estimate the concentration of testosterone in serum/plasma fall into six main categories: (1) gas chromatography/mass spectroscopy (Sabot, J. F., et al., *J. of Chromatography*, 339:233 (1985); Shinohara, Y., et al., *Biomedical and Environmental Mass Spectrometry*, 16:241 (1988); Furuta, T., et al., *J. of Chromatography*, 525:15 (1990); Fukushima, S., et al., *J. of Chromatography*, 565:35 (1991); Wudy, S. A., et al., *Steroids*, 57:319 (1992)); (2) isotope dilution mass spectrometry (Siekmann, L., *J. Steroid Biochem.*, 11:117 (1979); Moneti, G., et al., *J. Steroid Biochem.*, 27(1–3):53 (1987)); (3) thin laver chromatography (Vingler, P., et al., *J. of Chromatography*, 571:73 (1991)); (4) chemiluminescence (Syropoulos, A. B., et al., *Analytica Chimica Acta*, 239:195 (1990); Stabler, T. V., et al., *Clin. Chem.*, 37(11):1987 (1991); Van Dyke and Van Dyke, 1991); (5) high-performance liquid chromatography (Suzuki, Y., et al. *J. of Chromatogr.*, 426:33 (1988); Erkoc, F. U., et al., *J Chromatogr. Sci.*, 27:86 (1989); Ueshiba, H., et al., *Clin. Chem.*, 37(8):1329 (1991); (6) enzyme-linked immunoassays (Hosada, H., et al., *Chem. Pharm. Bull.*, 28(10):3035 (1980); Marcus, G. J., et al., *Steroids*, 46(6):975 (1985); Ali, E., et al., *J. Immunol. Methods*, 147:173 (1992); Sengupta, J., et al., *J. Immunol. Methods*, 147:181 (1992); Dhar, T. K., et al., *J. Immunol. Methods*, 147:167 (1992); Rassasie, M. J., et al., *Steroids*, 57:288 (1992); Rassasie, M. J., et al., *Steroids*, 57:112 (1992); Boehringer Mannheim GmbH, 1992); and finally (7) radioimmunoassay (Rao, P. N., et al., *J. Steroid Biochem.*, 9:539 (1978); Hosada, H., et al., *J. Steroid Biochem.*, 10:513 (1979); Cekan, S. Z., *J. Steroid Biochem.*, 11:1629 (1979); ICN Biomedicals, Inc., "RSL $^{125}$I Testosterone," Package Insert, Revision No. 4, January 1983; Diagnostics Products Corporation, "Coat-A-Count Total Testosterone," Package Insert, V 116, January 1992.).

The development since the 1960's of extremely sensitive and specific radioimmunoassays (RIAs) revolutionized the quantification of steroids. Because of their speed, simplicity and relatively low cost, the RIA approach is often used. This trend has been greatly encouraged by the availability of convenient, reliable commercial kits.

The commercially available testosterone assays are primarily "direct" radioimmunoassays which do not require organic extraction. In the RIAs, a limited amount of specific antibody is reacted with the hormone. $^{125}$I-labeled testosterone competes for a fixed time with testosterone in the patient sample. After separation of the bound from the free hormone, the amount of radioactivity in the bound fraction is quantified and used to construct a standard curve against which the unknown samples are measured. The commercial assays for testosterone vary in the method used to separate the bound and free hormone.

Examples of commercially available RIAs include the Coat-A-Count Total Testosterone Assay from Diagnostic Products Corporation (DPC) and the ICN Biomedicals, Inc. RSL $^{125I}$I-Testosterone kit. The DPC kit utilizes a solid-phase separation procedure: (1) testosterone-specific antibody is immobilized to the wall of a polypropylene tube, (2) $^{125}$I testosterone competes with analyte in the patient specimen, (3) the tube is decanted to separate the bound from the free hormone.

The RSL kit utilizes a liquid phase separation procedure: 1) testosterone-specific antibody is not bound to a solid phase, but is free in solution, 2) $^{125}$I-testosterone competes with analyte in the patient specimen, 3) a precipitating antiserum (second antibody) is then added to precipitate the testosterone-specific antibody:hormone and separate the bound from free hormone.

The above-described RIA methods suffer from the following disadvantages: 1) individuals must use radiological protection procedures; 2) radioactive waste must be disposed; 3) the labeled reagents used have short half-lives. For these reasons alternative immunoassay methods have been sought.

In contrast to the RIA methods, recently introduced microparticle enzyme immunoassays (MEIAs) are relatively new test methods being used in the physician's office and hospital settings. In this method, antibody is bound to the latex particles in suspension and the corresponding analyte being evaluated is then specifically bound. The particles are then passed through a glass fiber filter system. The particles adsorb to the glass fiber filter and the unbound analyte is washed through the glass fiber filter. For small molecular weight analytes such as steroids, the amount of analyte is determined by quantifying the number of antibody molecules which have not bound analyte. This is achieved by the addition of a hapten labeled conjugate. A substrate for the enzyme is then added which generates fluorescence rates which are inversely proportional to the amount of analyte in the sample.

Another nonisotopic homogeneous technique that has gained widespread use is fluorescent polarization. This technology was not known for the quantification of testosterone. Fluorescent polarization techniques are based on the principle that a fluorescent labeled compound when excited by linearly polarized light will emit fluorescence having a degree of polarization inversely related to its rate of rotation. Therefore, when a fluorescent labeled tracer-antibody complex is excited with linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate and the molecules are more randomly oriented, therefore, the emitted light is depolarized. Thus, fluorescent polarization provides a quantitative means for measuring the amount of tracer-antibody conjugate produced in a competitive binding immunoassay.

SUMMARY OF THE INVENTION

One aspect of the present invention presents novel Position 1 labeled reagents and immunogens; antibodies against Position 1 immunogens; and the novel starting material, 1-α-(n'-carboxyalkyl) testosterone, for making the novel Position 1 labeled reagents and immunogens.

Another aspect of the invention presents assays for detecting and quantifying testosterone in a test sample. These assays either use only the above reagents or the above reagents in combination with Position 6 labeled reagents or antibodies against Position 6 immunogens. The preferred assays are immunoassays which use Position 1 labeled reagents and antibodies raised with Position 6 immunogens. Preferably, the assays are microparticle enzyme immunoassays and fluorescence polarization immunoassays which combine the specificity of an immunoassay with the speed and convenience of homogeneous methods to provide the precise and reliable quantification of testosterone in a test sample.

Another aspect of the invention presents synthetic procedures for preparing the novel Position 1 immunogens, antibodies against the novel Position 1 immunogens, Position 1 labeled reagents, and the starting material for making the Position 1 immunogens and labeled reagents.

(3'-carboxypropyl) testosterone to alkaline phosphatase according to the synthetic method of the present invention.

Figure 11:
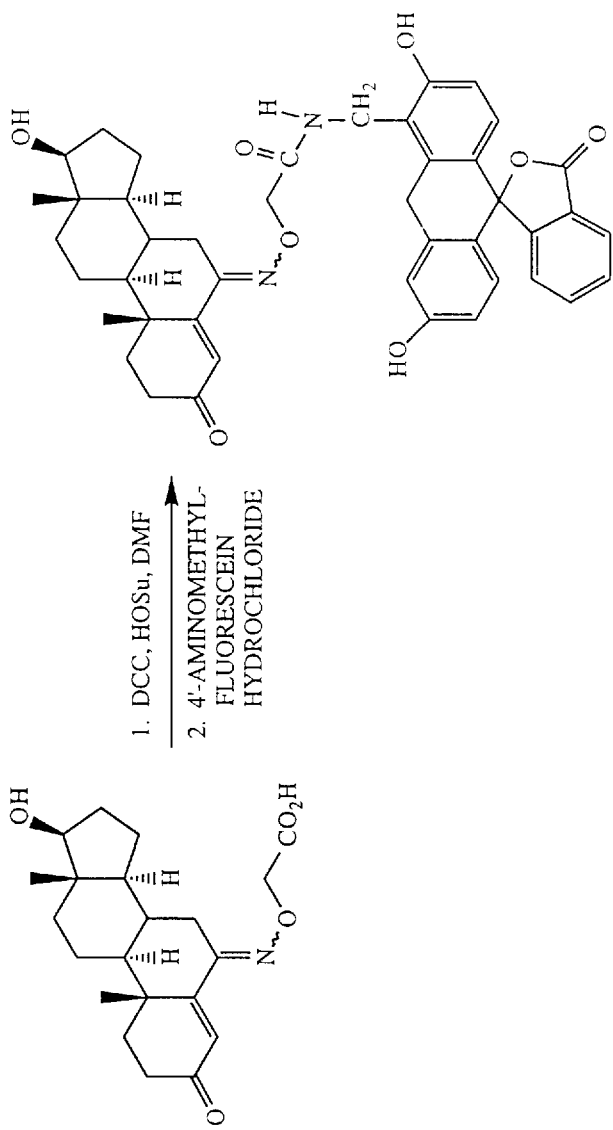

FIG. 11 illustrates the synthetic pathway for the preparation of a tracer of the present invention by coupling 6-(O-carboxymethyl)-oxime testosterone to 4'-aminomethylfluorescein according to the synthetic method of the present invention.

Figure 12:
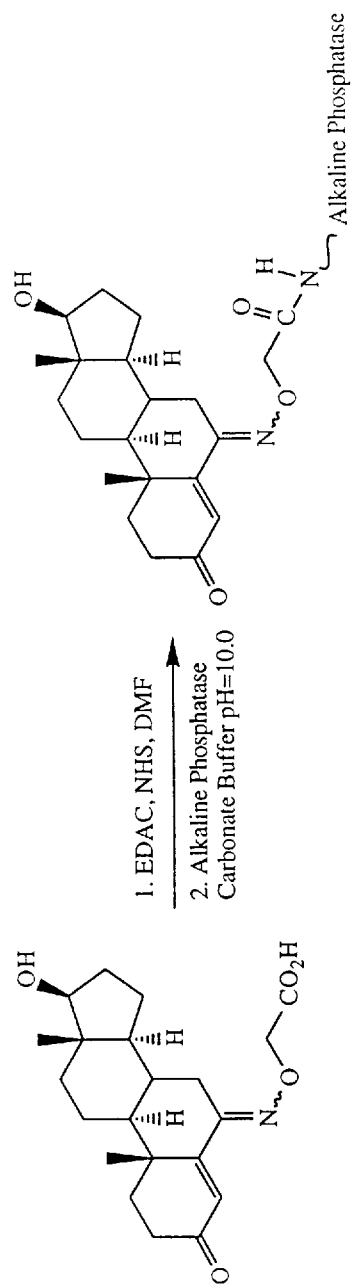

FIG. 12 illustrates the synthetic pathway for the preparation of a tracer of the present invention by coupling 6-(O-carboxymethyl)-oxime testosterone to alkaline phosphatase according to the synthetic method of the present invention.

Figure 13:
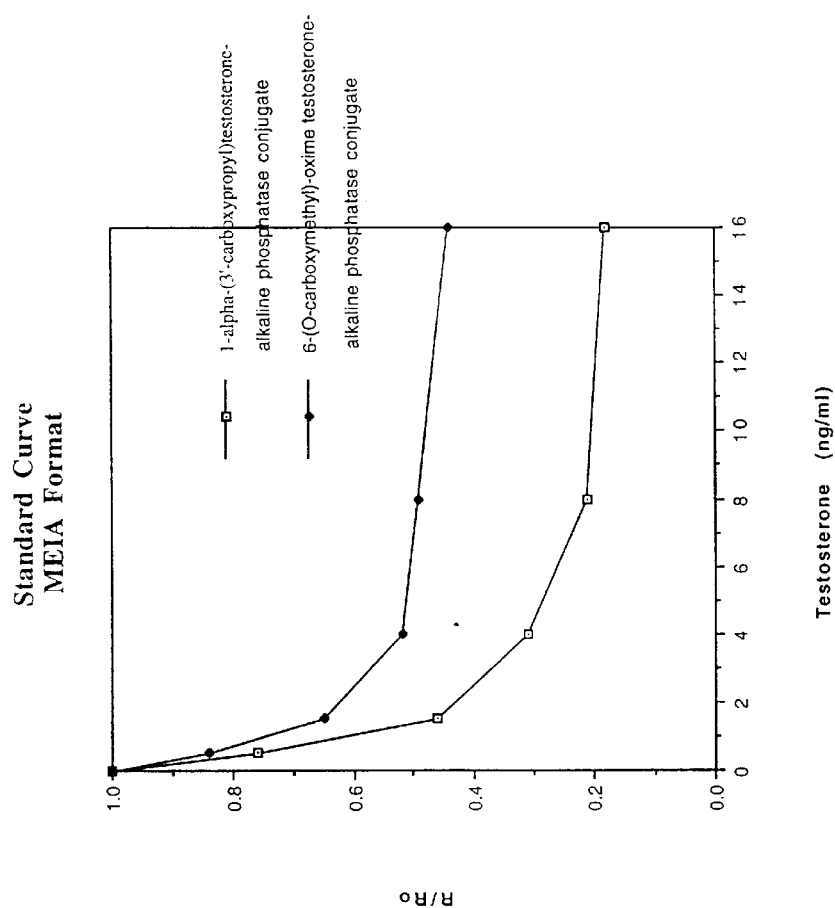

FIG. 13 illustrates a standard curve using the 1-α-(3'-carboxypropyl) testosterone:alkaline phosphatase labeled reagent (Example 10) and the 6-(O-carboxymethyl)-oxime testosterone:alkaline phosphatase labeled reagent (Example 12).

DETAILED DESCRIPTION OF THE INVENTION

The present invention presents novel Position 1 labeled reagents and immunogens, and antibodies against Position 1 immunogens. The novel starting material for making the Position 1 labeled reagents and immunogens is also presented. The invention also presents assays for detecting and quantifying testosterone in a test sample. These assays either use only the above reagents or the above reagents in combination with Position 6 labeled reagents or antibodies against Position 6 immunogens. The preferred assays are immunoassays which use Position 1 labeled reagents and antibodies raised with Position 6 immunogens. Preferably, the assays are microparticle enzyme immunoassays and fluorescence polarization immunoassays which combine the specificity of an immunoassay with the speed and convenience of homogeneous methods to provide the precise and reliable quantification of testosterone in a test sample. Another aspect of the invention presents synthetic procedures for preparing the Position 1 immunogens, labeled reagents, and their starting material, and the antibodies raised with the Position 1 immunogens.

The abbreviations used herein are:
Ar=Argon;
BSA=Bovine serum albumin;
$CDCl_3$=Deuterium chloroform.
DCC=1,3-Dicyclohexylcarbodiimide;
DMF=Dimethylformamide;
EDA-BOC=N-Butyloxycarbonyl ethylenediamine
EDAC=1-ethyl-3-(3-dimethylaminopropyl)-carbodiimide;
EtOAC=Ethyl acetate;
EtOAc/Hex=Ethyl acetate/Hexane;
EtOH=Ethanol;
HF=Hydrofluoric acid
HOSu=N-hydroxysuccinimide;
KLH=Keyhole Limpet Hemocyanin;
$Me_2S$=Dimethyl sulfide
MeOH=methanol;
N-Boc=N-t-Butyloxy carbonyl;
NHS=N-hydroxysuccinimide;
OTBDMS=t-Butyldimethylsilyl ether;
TBDMS=t-Butyldimethylsilyl;
TBDMSC=t-Butyldimethylsilyl chloride;
t-BuOH=t-Butanol;
TFA=Trifluoroacetic acid;
THF=Tetrahydrofuran;
TLC=Thin Layer Chromatography;
TNBS=Trinitrobenzylsulfonic acid;
1-α-(3'-carboxypropyl) testosterone-EDA=1-α-(3'-carboxypropyl) testosterone-ethylenediamine;
4-Androsten- 17β-ol-3-one=testosterone 5-CFL=5-Carboxyfluorescein; and
6-CFL=6-Carboxyfluorescein.

Further, "Position 1 immunogen" is defined as an immunogen wherein an immunogenic carrier protein is attached via a linker arm to position 1 of the steroid ring of the testosterone molecule.

"Position 6 immunogen" is defined as an immunogen wherein an immunogenic carrier protein is attached via a linker arm to position 6 of the steroid ring of the testosterone molecule.

"Position 1 labeled reagent" is defined as a labeled reagent wherein a label is attached via a linker arm to position 1 of the steroid ring of the testosterone molecule.

"Position 6 labeled reagent" is defined as a labeled reagent wherein a label is attached via a linker arm to position 6 of the steroid ring of the testosterone molecule.

Position 6 immunogens are known in the art. On the other hand, to the best of applicants' knowledge, Position 1 labeled reagents and Position 1 immunogens are unknown in the art. Thus, the Position 1 labeled reagents and immunogens disclosed herein and the chemistry for synthesizing them represent another aspect of the invention disclosed herein. M. Kocor et al., Polish J. Chem., 83:149–155 (1979) discloses (COOH) linked to position 1 of testosterone. However, Kocor et al. do not disclose immunogens or labeled reagents and their uses in immunoassays, least of all in assays for testosterone. Additionally, Kocor et al disclose a different synthetic method from that of the current invention.

The present invention also presents a novel starting material for the making of the novel Position 1 immunogens and labeled reagents. The methods of making the novel starting material are also presented. The novel starting material is 1-α-(n'-carboxyalkyl) testosterone and its structural formula is shown below:

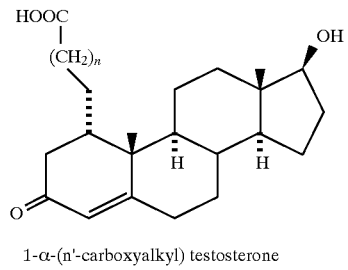

1-α-(n'-carboxyalkyl) testosterone

In the above formula, n is between 1 and 10, inclusively. Preferably, n is between 1 and 5, inclusively. More preferably, n is 3. "n'" is a numeral which is the same as that of "n".

The preferred starting material is 1-α-(3'-carboxypropyl) testosterone, which has the following structural formula:

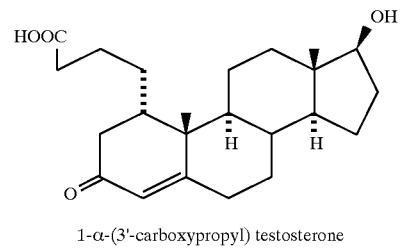

1-α-(3'-carboxypropyl) testosterone

The present invention also presents a novel method for making the novel starting material.

The above novel Position 1 labeled reagents and antibodies rasied agaisnt the Position 1 immunogens are useful in immunoassays for testosterone; they can be used in the same assay or can be combined with other labeled reagents or antibodies. The preferred assays use Position 1 labeled reagents and antibodies raised with Position 6 immunogens. According to the present invention, the detection and specific quantification of testosterone is accomplished by first contacting a test sample with a labeled reagent and an antibody reagent, either simultaneously or sequentially in either order, and then measuring the amount of the labeled reagent which either has or has not participated in a binding reaction with the antibody reagent as a function of the amount of testosterone in the test sample.

The test sample can be any naturally occurring body fluid or tissue, or an extract or dilution thereof, and includes, but is not intended to be limited to whole blood, serum, plasma, urine, and saliva.

In particular, the present invention relates to immunogens, antibodies prepared from such imnmunogens, and labeled reagents for use in microparticle enzyme immunoassays (MEIAs) and fluorescence polarization immunoassays (FPIAs) for the detection, and preferably the specific quantification of testosterone.

I. Labeled Reagents

The preferred Position 1 and Position 6 labeled reagents of the present invention have the following general formulae, respectively:

FORMULA 1
GENERAL STRUCTURE OF THE POSITION 1 LABELED REAGENT

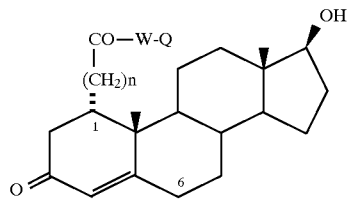

FORMULA 2
GENERAL STRUCTURE OF THE POSITION 6 LABELED REAGENT

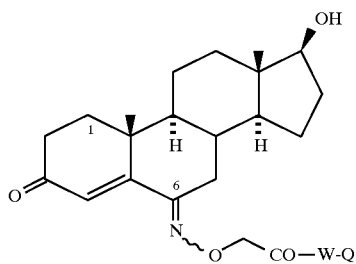

In Formula 1, n is between 1 and 10, inclusively. Preferably, n is between 1 to 5, inclusively. More preferably, n is 3.

In Formulae 1 and 2, Q is a detectable moiety. Q is preferably selected from the group consisting of enzymes, fluorescent molecules, and chemiluminescent molecules. Q is preferably a fluorescent moiety or enzyme. In the preferred labeled reagent, Q is a fluorescein derivative chosen from the group consisting of aminomethyl fluoresceins such as 4'-aminomethylfluorescein, 5-aminomethylfluorescein, and 6-aminomethylfluorescein; carboxyfluoresceins such as 5-carboxyfluorescein, 6-carboxyfluorescein; aminofluoresceins such as 5- and 6-aminofluorescein; thioureafluorescein; and methoxytriazinolyl-aminofluorescein. In a MEIA format, preferable examples of Q are the enzymes alkaline phosphatase, horseradish peroxidase, beta-galactosidase, and beta-lactamase. Examples of Q as chemiluminescent molecules are: luminol, acridinium sulfonamide, and acridinium esters.

W is a linking moiety preferably consisting of from 0 to 50 carbons and heteroatoms, including not more than ten heteroatoms, arranged in a straight or branched chain or cyclic moiety or any combination thereof, saturated or unsaturated, with the provisos that: (1) not more than two heteroatoms may be directly linked, (2) W cannot contain —O—O— linkages, (3) the cyclic moieties contain 6 or fewer members, and (4) branching may occur only on carbon atoms. Heteroatoms may include nitrogen, oxygen, and sulfur. When a Position 1 labeled reagent (as represented by Formula 1) is used in an assay with an antibody raised with the immunogen of Formulae 5 or 6, the specific chemical structure of W can be the same or different from that of the X of the immunogen. Similarly, when the Position 6 labeled reagent (as represented by Formula 2) is used in an assay with an antibody raised with an immunogen of Formula 5 or 6, the specific chemical structure of W can be the same or different from that of the X of the immunogen. More preferably, W consists of between 0 to 10 carbons and heteroatoms. Examples of W are: alkylene, arylalkylene and alkylene substituted cycloalkylene groups. It shall be noted that, according to the definition herein, W can be zero, i.e. when the carbon and heteroatoms are zero. If W=0, then no linking moiety exists, which indicates that Q is directly linked to the testosterone derivative.

A preferred Position 1 labeled reagent which is fluorescein labeled is represented by Formula 3 below:

FORMULA 3
STRUCTURE OF THE PREFERRED FLUORESCEIN-LABELED TESTOSTERONE REAGENT

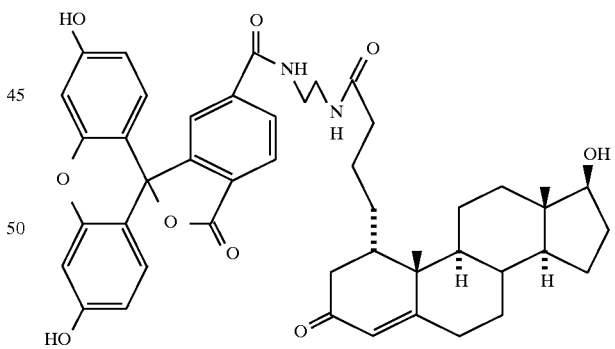

For fluorescence polarization assay the labeled reagent of Formula 3 is preferred. Aminomethylfluorescein could be used to prepare the reagent of Formula 3, as described by Kirkemo et al., U.S. Pat. No. 4,510,251, "Fluorescent Polarization Assay for Ligands using Aminomethylfluorescein Derivatives as Tracers", issued Apr. 9, 1985; and Mattingly, U.S. patent application Ser. No. 07/859,775, "5(6)-Methyl-Substituted Fluorescein Derivatives", filed Mar. 30, 1992.

A preferred Position 1 labeled reagent which is enzyme labeled is represented by the following formula:

FORMULA 4
STRUCTURE OF THE MOST PREFERRED ENZYME-LABELED TESTOSTERONE REAGENT

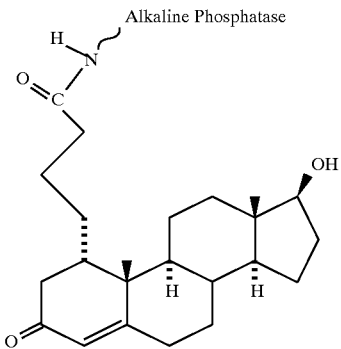

Other Position 1 labeled reagents are shown in the Examples below.

II. Immunogens

The preferred Position 1 and 6 immunogens are represented by structural Formulae 5 and 6 below, respectively:

FORMULA 5
GENERAL STRUCTURE OF POSITION 1 IMMUNOGEN

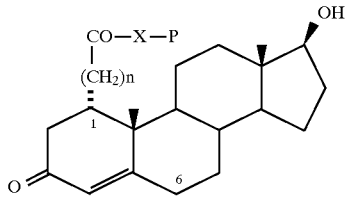

FORMULA 6
GENERAL STRUCTURE OF POSITION 6 IMMUNOGEN

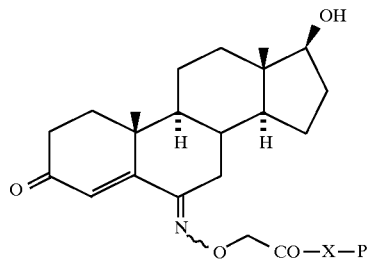

In Formulae 5 and 6, P is an immunogenic carrier material and X is a linking moiety. The terms linking moiety, tether, spacer, spacer arm, and linker are used interchangeably and are meant to define any covalently bound chemical entity that separates one defined substance (such as a hapten) from a second defined substance (such as an immunogenic carrier or detectable moiety).

In the present invention, X is a linking moiety preferably consisting of from 0 to 50 carbons and heteroatoms, including not more than ten heteroatoms, arranged in a straight or branched chain or cyclic moiety or any combination thereof, saturated or unsaturated, with the provisos that: (1) not more than two heteroatoms may be directly linked, (2) X cannot contain —O—O— linkages, (3) the cyclic moieties contain 6 or fewer members, and (4) branching may occur only on carbon atoms. Heteroatoms may include nitrogen, oxygen, and sulfur. Examples of X are: alkylene, arylalkylene and alkylene substituted cycloalkylene groups. It shall be noted that, according to the definition herein, X can be zero, i.e. when the carbon and heteroatom are zero. If X=0, then no linking moiety exists, which indicates that P is directly linked to the testosterone derivative in Formulae 5 and 6. More preferably, X consists of between 0 to 10 carbons and heteroatoms.

In Formula 5, "n" can be a number between 1 to 10, inclusively. Preferably, n is between 1 to 5, inclusively. More preferably, n is 3.

As one skilled in the art would realize, the ratio of the testosterone derivative to the immunogenic carrier in Formulae 5 and 6 are not limited to the ratio of one to one. The ratio of testosterone derivative to immunogenic carrier is defined by the number of chemically available functional groups on the immunogenic carrier and controlled by the ratio of the two materials in the synthesis. The degree of substitution on P by the testosterone derivative can vary between 1 to 100%, inclusively, of the available functional groups on the immunogenic carrier. The level of substitution is preferably between 10% to 95%, inclusively; and more preferably, between 15% to 85%, inclusively.

As would be understood by one skilled in the art, the immunogenic carrier material P can be selected from any of those conventionally known in the art, and in most instances will be a protein, polypeptide or peptide, although other materials such as carbohydrates, polysaccharides, lipopolysaccharides, poly(amino) acids, nucleic acids, and the like, of sufficient size and immunogenicity can also be employed. Preferably, the immunogenic carrier material is a protein such as bovine serum albumin (BSA), keyhole limpet hemocyanin (KLH), thyroglobulin, and the like.

In the more preferred immunogen, P is bovine serum albumin (BSA) and X is 0 as shown in structural Formula 7 below:

FORMULA 7
STRUCTURE OF THE MORE PREFERRED TESTOSTERONE IMMUNOGEN

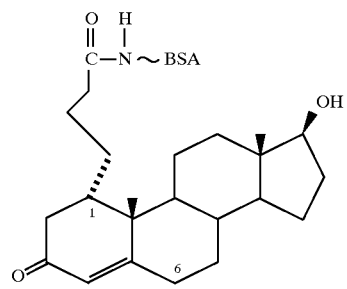

III. Preparation of the Position 1 Labeled Reagent and Immunogen

Both the Position 1 labeled reagent and imniunogen can be synthesized using the novel starting material, 1-α-(n'-carboxyalkyl) testosterone, and more preferably, 1-α-(3'-carboxypropyl) testosterone.

The steps for making 1-α-(n'-carboxyalkyl) testosterone are as follows: the starting material, 1,4-androstandien-17β-ol-3-one (boldenone), is protected by a TBDMS group at the 17 position followed by alkylation with [n'+1]-alkenylmagnesium bromide to produce 1-[n'+1]-alkenyl-4-Androsten- 17β-ol-3-one-t-butyldimethylsilyl ether. Ozonolysis of this compound followed by oxidation with sodium hypochloride gave 1-α-(n'-carboxyalkyl)-4-Androsten-17β-ol-3-one-t-butyldimethylsilyl ether. Subsequently, the protective group at the 17 position is removed by treatment with aqueous hydrofluoric acid in acetonitrile to produce the desired hapten: 1-α-(n'-carboxyalkyl) testosterone.

The preferred 1-α-(n'-carboxyalkyl) testosterone is 1-α-(3'-carboxypropyl) testosterone. The synthesis of 1-α-(3'-carboxypropyl) testosterone is shown in Example 1 and FIG. 1 below. As used herein, when a compound shown in a Figure has a number designating it, the number is set off in bold and within bracket, e.g. in FIG. 1, [2] designates 1-(4'-pentenyl)-4-Androsten-17β-ol-3-one-t-butyldimethylsilyl ether.

Figure 1:
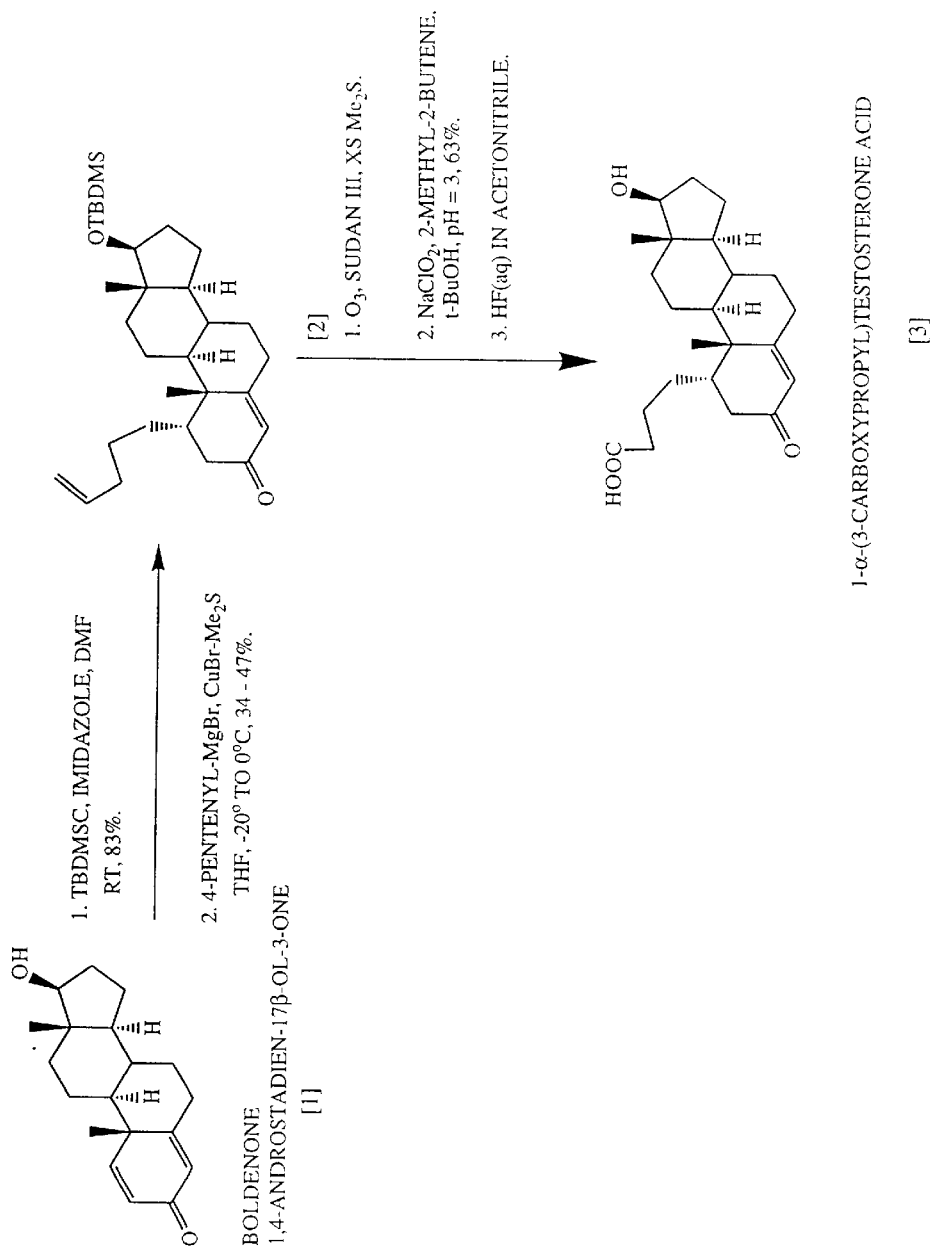
FIG. 1 illustrates the synthetic pathway for making 1-α-(3'-carboxypropyl) testosterone according to the synthetic method of the present invention.

As shown in Example 1 and FIG. 1, the starting material, 1,4-androstandien-17β-ol-3-one (boldenone), was protected by a TBDMS group at the 17 position followed by alkylation with 4-pentenylmagnesium bromide to afford 1-(4'-pentenyl)-4-Androsten-17β-ol-3-one-t-butyldimethylsilyl ether [2] (FIG. 1). Ozonolysis of this compound followed by oxidation with sodium hypochloride gave 1-α-(3'-carboxypropyl)4-Androsten-17β-ol-3-one t-butyldimethylsilyl ether. Subsequently, the protective group at the 17 position was removed by treatment with aqueous hydrofluoric acid in acetonitrile to produce the desired hapten: 1-α-(3'-carboxypropyl) testosterone [3] (FIG. 1)

Starting with 1-α-(n'-carboxyalkyl) testosterone, and preferably 1-α-(3'-carboxypropyl) testosterone, the Position 1 labeled reagents and immunogens can be synthesized as follows:

A. Preparation of the Preferred Novel Position 1 Labeled Reagents

The preferred Position 1 labeled reagents with the structural formula of Formula 1, can be synthesized from 1-α-(n'-carboxyalkyl) testosterone by: (a) selectively activating the 1-α-(n'-carboxyalkyl) group of testosterone; next (b) coupling the testosterone derivative with a selected detectable moiety; and finally (c) separating uncoupled testosterone from testosterone coupled to the detectable moiety.

More specifically, the above Position 1 labeled reagent can be synthesized by: (a) activating the 1-α-(n'-carboxyalkyl) group of testosterone with 1-ethyl-3-(3-dimethylaminopropyl)-carbodiimide and N-hydroxysuccinimide; followed by (b) coupling the activated ester to a detectable moiety under basic conditions; and finally (c) separating the uncoupled testosterone from the testosterone-detectable moiety complex or the detectable moiety by gel permeation chromatography.

Preferably, in the above preparations, the 1-α-(n'-carboxyalkyl) testosterone is 1-α-(3'-carboxypropyl) testosterone. The preferred detectable moieties are enzymes and fluoresceins.

B. Preparation of the Novel and Preferred Position 1 Immunogens

The preferred Position 1 immunogen of Formula 5 may be produced starting with 1-α-(n'-carboxyalkyl) testosterone. For simplicity of discussion, the following discussion uses the preferred 1-α-(3'-carboxypropyl) testosterone as an illustration, though it would be clear to one skilled in the art that other 1-α-(n'-carboxyalkyl) testosterones may be used. According to the following scheme as shown in FIGS. 1–4 (and their corresponding Examples) and described below:

1-α-(3'-carboxypropyl) testosterone can be coupled to a protein carrier, according to methods known to those skilled in the art, by means of a bifunctional linker or by direct coupling methods. In the case where a bifunctional linker is used, v-x-y represents the following. v and y are functional groups, one of which can react with the carboxylate of 1 carboxypropyl testosterone and the other with chemically available functional groups on P. X is the linking moiety. Many bifunctional linkers are known to one skilled in this art. For example, heterobifunctional linkers are described in U.S. Pat. No. 5,002,883 to Bieniarz, et al., hereby incorporated by reference. These heterobifunctional linkers are preferred in some cases due to the specificity of their ends for one functional group or another. Likewise, for convenience in the synthesis, protected forms of the functional groups v- and -y, well known to those skilled in the art (see e.g. T. W. Greene and P. G. M. Wutts, *Protective Groups in Organic Synthesis*, 2nd ed. 1991, John Wiley and Sons, hereby incorporated by reference) may be used and deprotected at the desired time.

Generally, in the preparation of immunogens of the present invention, v is selected from the group consisting of —OH, -halogen (e.g. —Cl, —Br, —I), —SH, and —NHR'. R' is selected from H, alkyl, aryl, substituted aryl; y is chosen from the group consisting of: hydroxy (—OH), carboxy (—C(=O)OH), amino (—NH2), aldehyde (—CH(=O)), and azido (—N3). X is a linking moiety preferably consisting of from 0 to 50 carbon and heteroatoms, including not more than ten heteroatoms, arranged in a straight or branched chain or cyclic moiety or any combination thereof, saturated or unsaturated, with the provisos that: (1) not more than two heteroatoms may be directly linked, (2) X cannot contain —O—O— linkages, (3) the cyclic moieties contain 6 or fewer members, and (4) branching may occur only on carbon atoms. Heteroatoms may include nitrogen, oxygen, and sulfur. Examples of X are: alkylene, arylalkylene and alkylene substituted cycloalkylene groups. It shall be noted that, according to the definition herein, X can be zero, i.e. the carbon and heteroatom are zero. If X=0, then no linking moiety exists, which indicates that P is directly linked to the testosterone derivative in Formula 2.

Reaction of the 1 carboxypropyl derivative of testosterone with v-X-y produces tethered intermediate compound (II) having linking moiety X with a functional group y. The functional group -y, can be reacted in any of several ways, known to those skilled in the art, with the functional groups on an immunogenic carrier. It is frequently preferable to form amide bonds, which typically are quite stable. Amide bonds are formed by first activating the carboxylic acid moiety [y=(—C(=O)OH)] of the spacer arm by reaction with an activating reagent such as 1,3-dicyclohexylcarbodiimide and an additive such as N-hydroxysuccinimide. The activated form is then reacted with a buffered solution containing the immunogenic carrier materials. Alternatively, the carboxylic acid group may be converted, with or without isolation, into a highly reactive mixed anhydride, acyl halide, acyl imidazolide, or mixed carbonate and then combined with the immunogenic carrier materials. One of ordinary skill in the art will recognize that there are many reagents that can be used to form amide bonds other than those listed.

A spacer arm with a terminal amine (y=—NH$_2$) functionality can be transformed into a highly reactive N-hydroxysuccinimide urethane by reaction with N,N'-disuccinimidyl carbonate in a suitable solvent, such as acetonitrile or dimethylformamide. The resultant urethane is then reacted with the immunogenic carrier materials in a buffered, aqueous solution to provide an immunogen.

A spacer arm with a terminal aldehyde functionality [y=—CH(=O)] can be coupled to the immunogenic carrier materials in a buffered, aqueous solution and in the presence of sodium cyanoborohydride, by reductive amination according to methods known to those skilled in the art.

In a manner analogous to immunogens, spacer arms can be conjugated to solid supports having functional groups such as amino, hydroxyl or carboxyl groups that are reactive in a complementary sense with reactive groups on the spacer arm. The result is a solid phase which can be used to separate or purify antibodies against the hapten.

Thus the above testosterone derivatives can be coupled to immunogenic carrier materials P by various conventional techniques known in the art.

IV. Preparations of Position 6 Labeled Reagents and Immunogens

The Position 6 labeled reagents and immunogens can be synthesized using methods known in the art, such as those utilizing 6-(O-carboxymethyl)-oxime testosterone (whose structural formula is shown below) as the starting material:

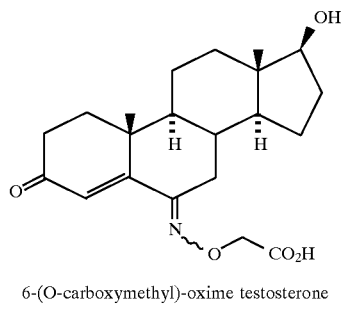

6-(O-carboxymethyl)-oxime testosterone

V. Production of Antibodies

The Position 1 and 6 immunogens disclosed herein can be used to prepare antibodies, both polyclonal and monoclonal, according to methods known in the art for use in an immunoassay system according to the present invention. Generally, a host animal, such as a rabbit, goat, mouse, guinea pig, or horse is injected at one or more of a variety of sites with the immunogen, normally in a mixture with an adjuvant. Further injections are made at the same site or different sites at regular or irregular intervals thereafter with bleedings being taken to assess antibody titer until it is determined that optimal titer has been reached. The antibodies are obtained by either bleeding the host animal to yield a volume of antiserum, or by somatic cell hybridization techniques or other techniques known in the art to obtain monoclonal antibodies, and can be stored, for example, at −20° C.

Besides whole immunoglobulins, antibodies herein include antigen binding fragments of the immunoglobulins. Examples of these fragments are Fab, F(ab')$_2$ and Fv. Such fragments can be produced by known methods.

Monoclonal antibodies can be produced by the method of Kohler and Milstein (Nature, 256, 495–497 (1975) by immortalizing spleen cells from an animal inoculated with the immunogen or a fragment thereof, usually by fusion with an immortal cell line (preferably a myeloma cell line), of the same or a different species as the inoculated animal, followed by the appropriate cloning and screening steps.

The antibodies may also be recombinant monoclonal antibodies produced according to the methods disclosed in Reading, U.S. Pat. No. 4,474,893, or Cabilly et al., U.S. Pat. No. 4,816,567. The antibodies may also be chemically constructed according to the method disclosed in Segel et al., U.S. Pat. No. 4,676,980.

Preferably, polyclonal and monoclonal antibodies of the present invention are produced with Position 1 immunogens having the structure represented in Formula 5. More preferably, the immunogen has the structure represented by Formula 7.

VI. Immunoassays Using the Novel Position 1 Labeled Reagents and Immunogens

The present invention found that surprisingly, excellent immunoassays for testosterone are obtained by using Position 1 labeled reagents and antibodies raised with Position 6 immunogens (as exemplified by the microparticle enzymatic immunoassay of Example 18). This finding is surprising because it is known to one of ordinary skill in the art that when preparing specific antibodies and complementary labeled haptens (such as the labeled reagents), one needs to consider the chemical structures of both the immunogen used to elicit the antibody response and the labeled hapten. Traditionally, one attaches the hapten to the carrier protein through a site on the hapten that is remote from the unique features of the hapten that are critical for achieving selective antibodies. Likewise, when preparing a labeled hapten capable of binding to such antibodies, it is customary to attach the label to the hapten through the same site as the carrier protein. Normally, the complementary labeled hapten is synthesized by attaching its label to the same site on the hapten as the immunogen used for attachment of its carrier protein, so as not to interfere with antibody binding to the critical features of the hapten.

The matching system which uses antibodies and enzyme conjugates derived from the same position of attachment to testosterone and the same linking arm did not allow for the construction of a standard curve in the range needed for quantification of testosterone in clinical samples. The present invention differs in that antibodies and enzyme conjugates were derived by attachment to different positions of testosterone using the same linking arm. This configuration has the advantages that a standard curve could be constructed in the range needed for the quantification of testosterone in clinical samples.

It is to be noted from Example 18 that the labeled reagent of the present invention alone can improve the performance of a testosterone assay. Thus, the assays or kits can use the labeled reagents of the present invention with antibodies, whether polyclonal or monoclonal, which recognize both testosterone and the labeled reagents of the present invention, and which are preferably antibodies that are raised by the immunogens of Examples 4 and 5. Additionally, to enable the performance of competitive immunoassays such as FPIA or MEIA, the tracers and testosterone must be able to competitively bind to the antibodies. Similarly, the immunogens are preferably derivatives or analogs of testosterone. The labeled reagents preferably do not bind or significantly bind endogenous immunoglobulins which may be found in the test sample, i.e. antibodies that are not intended to bind the labeled reagents, such that the binding interferes with the accuracy of the assay. It will be noted that the above labeled reagents and the immunogens that can be used to raise the antibodies for an assay or assay kit may have "W" and "X" (as shown in the above formulae 1,2, 5 and 6) that are the same or different.

A. Testosterone Assay utilizing Microparticle Enzyme Immunoassay

The concentration or level of testosterone in a test sample can be accurately quantified in a microparticle enzyme immunoassay (MEIA) by employing the reagents of the present invention. To perform an MEIA for the specific quantification of testosterone, calibration curves were generated for measuring the testosterone in a sample.

According to the present invention, it has been unexpectedly and surprisingly found that superior microparticle enzyme immunoassay results for the quantification of testosterone are obtained when employing the testosterone 1-α-(3'-carboxypropyl) labeled reagent (or tracer) of Formula 6.

In particular, it was unexpectedly and surprisingly found that the use of this labeled reagent was critical for the necessary sensitivity/precision of the assay. This advantage represents an advance over the prior art for the specific quantification of testosterone.

The amount of tracer bound to the antibody varies inversely to the amount of testosterone present in the test sample. Accordingly, the relative binding affinities of testosterone and the tracer to the antibody binding site are important parameters of the assay system.

Generally, microparticle enzyme techniques are based upon the principle of enzymatic cleavage of a substrate to yield a fluorescent end product. For competitive enzyme immunoassays, the amount of fluorescent product generated is inversely proportional to the amount of testosterone in the sample.

When performing a microparticle enzyme immunoassay for the specific quantification of testosterone according to the present invention, a test sample suspected of containing testosterone is contacted with antiserum or monoclonal antibodies prepared with immunogens according to the present invention, in the presence of labeled reagent of the present invention, which is capable of producing a detectable fluorescence response to the presence of antiserum or monoclonal antibodies prepared with immunogens according to the present invention.

B. Testosterone Assay utilizing Fluorescence Polarization Immunoassay

Generally, fluorescent polarization techniques are based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component with a relatively lower rate of rotation, will retain a relatively greater degree of polarization of emitted light than if in free solution.

When performing a fluorescent polarization immunoassay for the specific quantification of testosterone according to the present invention, a test sample suspected of containing testosterone is contacted with antiserum or monoclonal antibodies prepared with immunogens according to the present invention, in the presence of labeled reagent of the present invention, which is capable of producing a detectable fluorescence polarization response to the presence of antiserum or monoclonal antibodies prepared with immunogens according to the present invention. Plane polarized light is then passed through the solution to obtain a fluorescent polarization response and the response is detected as a measure of amount of testosterone present in the test sample.

The testosterone derivatives of the present invention are employed to prepare immunogens by coupling them to conventional carrier materials, and subsequently used to obtain antibodies. The testosterone derivatives of the present invention are also used to prepare labeled reagents which serve as the detection reagents in immunoassays for quantifying testosterone in a test sample.

The microparticle enzyme and fluorescence polarization assays can be conducted in commercially available automated instruments such as the IMx® instrument (available from Abbott Laboratories, Abbott Park, Ill., U.S.A.).

C. Other Assay Formats

In addition to microparticle enzyme and fluorescence polarization immunoassays, various other immunoassay formats can be followed for the quantification of testosterone according to the present invention. Such immunoassay system formats include, but are not intended to be limited to, competitive, sandwich and immunometric techniques. Generally, such immunoassay systems depend upon the ability of an immunoglobulin, i.e., a whole antibody or fragment thereof, to bind to a specific analyte from a test sample with a labeled reagent comprising an antibody of the present invention, or fragment thereof, attached to a label or detectable moiety. Such detectable labels include, but are not intended to be limited to, enzymes, radiolabels, biotin, toxins, drugs, haptens, DNA, RNA, liposomes, chromophores, chemiluminescers, colored particles and colored microparticles, fluorescent compounds such as aminomethylfluorescein, 5-fluoresceinyl, 6-fluoresceinyl, 5-carboxyfluorescein, 6-carboxyfluorescein, aminofluorescein, thioureafluorescein, and methoxytriazinolyl-aminofluorescein, and the like fluorescent derivatives.

Typically, the extent of binding in such immunoassay system formats is determined by the amount of the detectable moiety present in the labeled reagent which either has or has not participated in a binding reaction with the analyte, wherein the amount of the detectable moiety detected and measured can be correlated to the amount of analyte present in the test sample. For example, in a competitive immunoassay system, a substance being measured, often referred to as an analyte, competes with a substance of close structural similarity coupled to a detectable moiety, often referred to as a tracer, for a limited number of binding sites on antibodies specific to the portion or portions of the analyte and tracer with structural similarity, shared with an immunogen employed to produce such antibodies. An example of such an assay would involve: (a) contacting a test sample (suspected of having an analyte of interest) to a labeled reagent (i.e. a tracer) and an antibody which is capable of binding the labeled reagent and the analyte, to form a reaction solution; (b) incubating the reaction solution for a sufficient amount of time to allow the antibody to bind the labeled reagent and analyte, if present; and (c) measuring the amount of the labeled reagent in the reaction solution which is bound to said antibodies as a function of the amount of the analyte in the test sample. The labeled reagent and antibody can be added to the test sample simultaneously or sequentially, in no particular order. Preferably, the antibody is added to the test sample after the addition of the labeled reagent. The preferred assay utilizes Position 1 labeled reagent with antibodies raised with either Position 1 or Position 6 immunogen. Position 6 labeled reagent can also be used with antibodies raised with a Position 1 immunogen. Preferred examples of the immunogens and labeled reagents are shown in the Examples below.

V. Test Kits

A test kit according to the present invention comprises all of the essential reagents required to perform a desired immunoassay for the quantification of testosterone in a test sample. Examples of such immunoassays include a microparticle enzyme immunoassay and a fluorescent polarization immunoassay. The test kit is preferably presented in a commercially packaged form as a combination of one or more containers holding the necessary reagents, as a composition or admixture where the compatibility of the reagents will allow.

Particularly preferred is a test kit for the microparticle enzyme immunoassay quantification of testosterone in a test sample, comprising any tracer compounds and antibodies as described in this patent application for the quantification of testosterone. It is to be understood that the test kit can, of course, include other materials as are known in the art and which may be desirable from a user standpoint, such as buffers, diluents, standards, and the like.

The present invention will now be illustrated, but is not intended to be limited by the following examples.

The Examples describe the synthesis of:

(1) 1-α-(3'-carboxypropyl) testosterone, which is the starting material for the synthesis of Position 1 immunogens and labeled reagents (Example 1);

(2) Position 1 immunogens (Examples 2 and 3);

(3) Position 6 immunogens (Examples 4 and 5);

(4) Position 1 labeled reagents (Examples 6 to 10);

(5) Position 6 labeled reagents (Examples 11 and 12);

(6) Antibodies production and purification using immunogens of Examples 2 to (Examples 13–16);

(7) Coupling of antibodies produced in Example 16 to latex particles (Example 17); and (8) immunoassay using Position 6 immunogen of Example 4 and Position 1 labeled reagent of Example 10 (Example 18)

The invention described herein draws on both published and unpublished work. By way of example, such work consists of scientific papers, pending patent applications, and patents. All of the work cited in this application is hereby incorporated by reference.

The present invention has been described with reference to specific embodiments. However, this application is intended to cover those changes and substitutions which may be made by those skilled in the art without departing from the spirit and the scope of the appended claims.

EXAMPLE 1

This example (FIG. 1) illustrates the synthesis 1-α-(3'-carboxypropyl) testosterone, which corresponds to the formula:

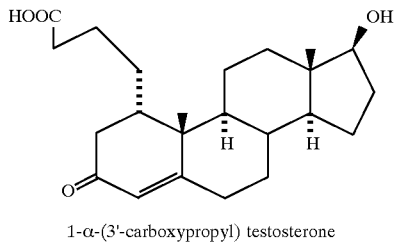

1-α-(3'-carboxypropyl) testosterone

To a stirred solution of t-butyldimethylsilyl chloride (11.0 g, 71 mmol) in 150 mL of dry DMF was added 1,4-androstadien-17β-ol-3-one (10.0 g, 35 mmol) and imidazole (9.5 g, 140 mmol) in one portion. The reaction mixture was stirred at room temperature for 4.5 hours. TLC [silica gel, EtOAc/Hex (10/90, v/v)] showed complete disappearance of starting material and some precipitate formed. The reaction mixture was poured into 300 mL of pentane and the organic phase was washed with ice cold 5% hydrochloric acid (100 mL×2), 5% sodium bicarbonate (100 mL×2), brine (100 mL×2) and dried over $MgSO_4$. Filtration followed by concentration of the filtrate under reduced pressure on a rotaevaporator to give a viscous oil. Purification by gravity column chromatography [500 g of silica gel, EtOAc/Hex (10/90 v/v) to EtOAc/Hex (20/80 v/v) as eluents] afforded 11.6 g (83%) of pure 1,4-androstadien-17β-3-one t-butyldimethylsilyl ether. $^1$H NMR (300 MHz, $CDCl_3$) δ 7.054 (d, J=10.30 Hz, 1H), 6.220 (dd, J=1.84 Hz, J=10.30 Hz, 1H), 6.063 (m, 1H), 3.545 (t, J=8.27 Hz, 1H), 2.600–2.300 (m, 2H), 2.000–0.700 (m, 13H), 1.237 (s, 3H), 0.879 (s, 9H), 0.779 (s, 3H), 0.000 (s, 6H); $^{13}$C NMR (75 MHz, $CDCl_3$) δ 186.30, 169.16, 155.84, 127.46, 123.84, 81.43, 52.73, 49.77, 43.64, 43.45, 36.74, 35.66, 33.23, 32.83, 30.79, 25.83 (3C), 23.68, 22.56, 18.75, 18.07, 11.41, −4.50, −4.84; mass spec (DCI, $NH_3$) 401 $(M+H)^+$, 418 $(M+NH_4)^+$.

4-PENTENYLMAGNESIUM BROMIDE

An oven-dried 250 mL 3-neck round bottom flask equipped with a stirbar, septa and a 250 mL addition funnel was charged with Mg turnings (4.30 g, 0.177 mmol) and the apparatus was purged with Ar while being heated with a heat gun. After cooling to room temperature, the Mg turnings were covered with 30 mL of anhydrous THF. A crystal of $I_2$ was added and as soon as the brown color of $I_2$ reaction mixture disappeared, a solution of 5-bromo-1-pentane (25 g, 0.168 mmol) in 50 mL of anhydrous THF was added dropwise over 2.5 hours with some warming of the reaction mixture. After addition was complete, the reaction mixture was stirred at room temperature for 2 hours and 70 mL of dry THF was added to dissolve the precipitated Grignard reagent. The resultant solution was cannulated under Ar into a dry septum-capped 200 mL brown bottle for storage at room temperature.

1-α-(4'-PENTENYL)-4-ANDROSTEN-17β-OL-3-ONE t-BUTYLDIMETHYLSILYL ETHER

An oven-dried 250 mL 3-necked round bottom flask was equipped with a stirbar and septa then charged with a 1.0M solution of 4-penten-1-yl magnesium bromide in THF (75 mL, 75 mmol) at −20° C. under Ar. To this rapidly stirred suspension was added CuBr-dimethyl sulfide complex (1.52 g, 7.4 mmol) in one portion. After 3 minutes of stirring, 1,4-androstadien-17β-3-one t-butyldimethylsilyl ether (4.42 g, 11.03 mmol) in 7 mL of dry THF was added through an addition funnel for approximately 3 minutes. Any precipitate in the addition funnel was washed down with a small amount of dry THF (3 mL). The flask was then warmed to 0° C. in an ice water bath with stirring for 15 minutes. The resulting blood-red solution was cooled to −78° C. (dry ice-acetone) and slowly quenched by the addition of 9N hydrochloric acid (deoxygenated by purging with Ar) to afford a yellow mixture. The mixture was poured into 150 mL of diethyl ether and 150 mL of brine. The organic phase was separated, washed with half saturated sodium bicarbonate (100 mL), brine (100 mL×2) and dried over $MgSO_4$. The crude product obtained after drying, filtration and evaporation of solvent was purified by gravity column chromatography [300 g of silica gel, EtOAc/Hex (10/90, v/v)] to yield 2.52 g (49%) of pure 1-α-(4'-pentenyl)-4-androsten-17β-ol-3-one t-butyldimethylsilyl ether. $^1$H NMR (300 MHz, $CDCl_3$) δ 6.000–5.500 (m, 2H), 5.100–4.900 (m, 2H), 3.581 (t, J=8.27 Hz, 1H), 2.800–0.700 (m, 24H), 1.301 (s, 3H), 0.888 (s, 9H), 0.760 (s, 3H), 0.000 (s, 6H); $^{13}$C NMR (75 MHz, $CDCl_3$) δ 199.10, 168.79, 138.49, 123.69, 114.64, 81.58, 50.34, 46.47, 43.21, 41.87, 41.70, 37.97, 36.71, 35.56, 33.75, 32.96, 30.86, 30.61, 26.73, 26.60, 25.84 (3C), 23.52, 20.51, 19.91, 18.08, 11.37, −4.47, −4.83; mass spec (DCI, $NH_3$) 471 $(M+H)^+$, 488 $(M+NH_4)^+$.

1-α-(3'-CARBOXYPROPYL)-4-ANDROSTEN-17βOL-3-ONE t- BUTYLDIMETHYLSILYL ETHER

To the solution of 1-α-(4'-pentenyl)-4-androsten-17β-ol-3-one t-butyldimethylsilyl ether (1.918 g, 4.07 mmol) in a mixture of $CH_2Cl_2$ (200 mL), MeOH (100 mL) and pyridine (2 mL) in a 500 mL 3-neck round bottom flask was added Sudan III solution (2 mL, 0.1% in EtOH) and the whole light pink solution was cooled to −78° C. with stirring. The reaction mixture was passed a stream of $O_3$ (generated at 90 V, 7.5 psi of $O_2$ and 0.2 lpm of flow rate) through a Pasteur pipette just below the surface of the solution. When the color of Sudan III disappeared, the addition of $O_3$ was halted and $N_2$ was gently bubbled into the solution to displace any excess of $O_3$. Dimethyl sulfide (4 mL, 54.3 mmol) was added to the resulting solution and the stirred mixture was allowed to warm to room temperature slowly overnight. TLC [silica gel, EtOAc/Hex (20/80, v/v)] showed complete consumption of starting material. The reaction mixture was evaporated under reduced pressure on a rotaevaporator and the residual material was co-evaporated twice with 100 mL of toluene to remove any traces of MeOH. The resulting residue was dissolved in 30 mL of t-BuOH, added 2-methyl-2-butene (6.7 mL, 63 mmol) and then added slowly, with stirring, an oxidant solution prepared freshly by addition of sodium chlorite (920 mg, 8.14 mmol) to mL of phosphate buffer (pH=3.3, 0.20M). After 30 minutes of stirring at room temperature, the oxidation reaction was complete. The reaction mixture was evaporated on a rotaevaporator to dryness and the residue was shaken with a mixture of 300 mL of brine/300 mL of EtOAc and pH was adjusted to pH=3. The organic layer was separated, washed with sodium sulfite solution (300 mL, 2% w/v, pH=4), dried over $MgSO_4$, filtered and evaporated to a crude material which was purified by gravity column chromatography [120 g of silica gel, $CHCl_3$/MeOH (95/5)] to afford an oil. Recrystallation from 30 mL of $CH_3CN$ yielded 863 mg (43%) of 1-α-(3'-carboxypropyl)-4-androsten-17β-ol-3-one t-butyldimethylsilyl ether as solid material. $^1H$ NMR (300 MHz, $CDCl_3$) δ 5.701 (s, 1H), 3.581 (t, J=8.09 Hz, 1H), 2.700–2.300 (m, 2H), 2.320 (t, J=6.98 Hz, 2H), 2.000–0.800 (m, 20H), 1.310 (s, 3H), 0.888 (s, 9H), 0.760 (s, 3H), 0.000 (s, 6H); $^{13}C$ NMR (75 MHz, $CDCl_3$) δ 198.84, 178.46, 168.80, 123.71, 81.53, 50.29, 46.49, 43.21, 41.82, 41.69, 37.91, 36.61, 35.56, 33.85, 32.96, 30.87, 30.60, 26.77, 25.86, 23.52, 22.67, 20.51, 19.93, 18.08, 11.36, −4.47, −4.78; mass spec (DCI, $NH_3$) 489 (M+H)$^+$, 506 (M+NH4)$^+$.

1-α-(3'-CARBOXYPROPYL) TESTOSTERONE

To the stirred suspension of 1-α-(3'-carboxypropyl)-4-androsten-17β-3-one t-butyldimethylsilyl ether (841 mg, 1.76 mmol) in 50 mL of $CH_3CN$ was added 10 mL of a freshly prepared 5% (v/v) of 48% HF in $CH_3CN$. The mixture gradually became homogeneous upon stirring and was complete by TLC [silica gel, $CH_2Cl_2$ (93/7, v/v) after 1 hour. The reaction mixture was poured into 300 mL of brine and extracted with 300 mL of EtOAc. The organic layer was separated, washed with brine (300 mL×2), dried over $MgSO_4$, filtered and evaporated on a rotaevaporator to give crude material which was purified by gravity column chromatography [120 g of silica gel, $CHCl_3$/MeOH (90/10, v/v)] to yield 553 mg (86%) of pure 1-α-(3'-carboxypropyl) testosterone. $^1H$ NMR (300 MHz, $CDCl_3$) δ 5.704 (s, 1H), 3.669 (t, J=8.46 Hz, 1H), 2.700–2.300 (m, 2H), 2.309 (t, J=6.98 Hz, 2H), 2.150–0.800 (m, 21H), 1.308 (s, 3H), 0.801 (s, 3H); $^{13}C$ NMR (75 MHz, $CDCl_3$) δ 199.14, 178.41, 168.92, 123.68, 81.48, 50.65, 46.36, 42.84, 41.79, 41.62, 37.86, 36.16, 35.48, 33.90, 32.91, 30.52, 30.32, 26.67, 23.37, 22.64, 20.43, 19.86, 11.13; mass spec (DCI, $NH_3$) 375 (M+H)$^+$, 392 (M+NH$_4$)$^+$.

EXAMPLE 2

Figure 2:
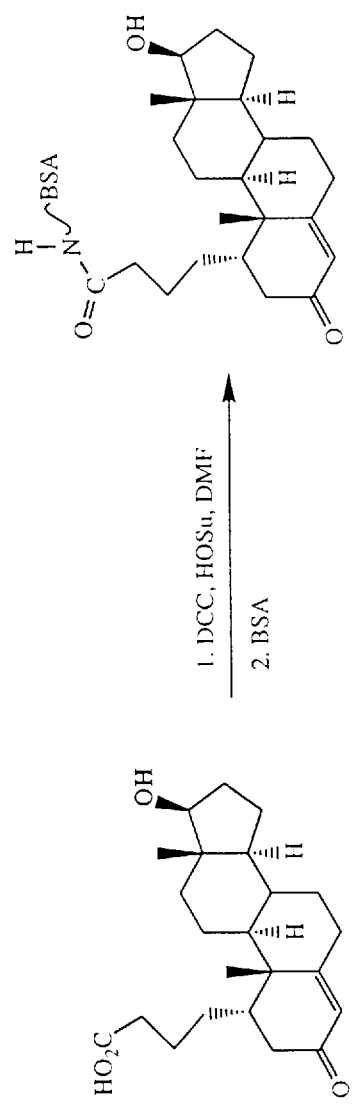
FIG. 2 illustrates the synthetic pathway for the preparation of an immunogen of the present invention by coupling 1-α-(3'-carboxypropyl) testosterone to bovine serum albumin (BSA) according to the synthetic method of the present invention.

This example illustrates conjugation of 1-α-(3'-carboxypropyl) testosterone to bovine serum albumin (FIG. 2).

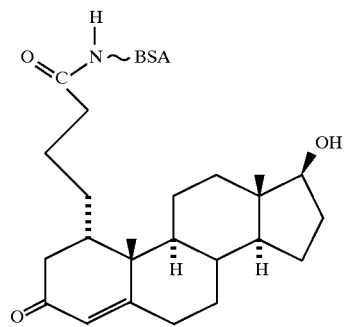

To the stirred solution of 1-α-(3'-carboxypropyl)-4-androsten-17β-3-one, TBDMS-ether(64 mg, 0.17 mmol) and HOSu (24 mg, 0.21 mmol) in 1 mL of dry DMF was added DCC (35 mg, 0.17 mmol) in one portion. The whole homogeneous solution became cloudy after stirring for 30 minutes. The reaction mixture was stirred for 16 hours at room temperature and monitored by TLC (silica gel, 100% ethyl acetate) for the formation of activated ester. The activated ester mixture was filtered through a disposable pipette filled with cotton plug and the solid was washed with 1 mL of dry DMF. A solution of bovine serum albumin (BSA, 293 mg) in 5 mL of phosphate buffer (pH=7.80) was added dropwise to the filtered solution of activated ester. After being stirred at room temperature for 16 hours, the reaction mixture was transferred to a dialysis membrane tubing (SPECTRA/POR*2, 797925, Cat. D1614-12, Size 25 mm, Dia. 15.9 mm) and the tube was dialyzed against phosphate buffer (4 L, 0.1M, pH=7.80) for 6 hours. The tube was then dialyzed with distilled water 4 L at: 7 hours, 17 hours, 7 hours, 17 hours, 7 hours, 17 hours, 7 hours. The protein solution was lyophilized and packed. TNBS titration showed 56% substitution of amino groups

EXAMPLE 3

Figure 3:
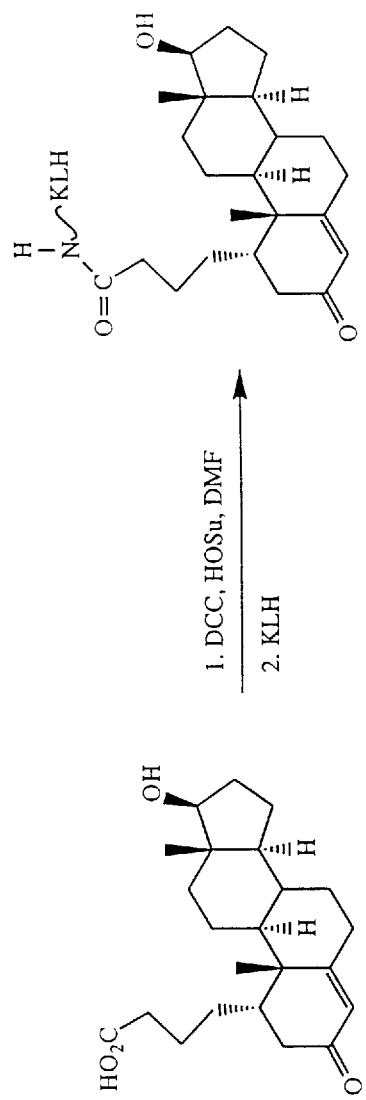
FIG. 3 illustrates the synthetic pathway for the preparation of an immunogen of the present invention by coupling 1-α-((3'-carboxypropyl) testosterone to keyhole limpet hemocyanin (KLH) according to the synthetic method of the present invention.

This example illustrates conjugation of 1-α-(3'-carboxypropyl) testosterone to keyhole limpet hemocyanin (FIG. 3).

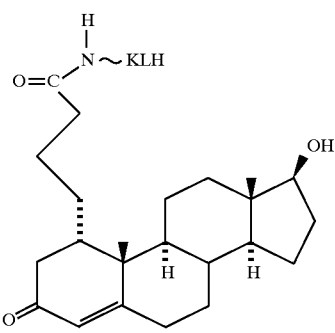

To the stirred solution of 1-α-(3'-carboxypropyl)-4-androsten-17β-3-one, TBDMS-ether (64 mg, 0.17 mmol) and HOSu (24 mg, 0.21 mmol) in 1 mL of dry DMF was added DCC (35 mg, 0.17 mmol) in one portion. The whole homogeneous solution became cloudy after stirring for 30 minutes. The reaction mixture was stirred for 16 hours at room temperature and monitored by TLC (silica gel, 100% ethyl acetate) for the formation of activated ester. The activated ester mixture was filtered through a disposable pipette filled with cotton plug and the solid was washed with 1 mL of dry DMF. A solution of keliole limpet hemocyanin (KLH, 292 mg) in 10 mL of phosphate buffer (pH=7.80) was added to the filtered solution of activated ester dropwise. After stirring at room temperature for 16 hours, the reaction mixture was transferred to a dialysis membrane tubing (SPECTRA/POR*2, 797925, Cat. D1614-12, Size 25 mm, Dia. 15.9 mm) and the tube was dialyzed against phosphate buffer (4 L, 0.1M, pH=7.80) for 6 hours. The tube was then dialyzed with distilled water 4 L at: 7 hours, 17 hours, 7 hours, 17 hours, 7 hours. The protein solution was lyophilized and packed.

EXAMPLE 4

Figure 4:
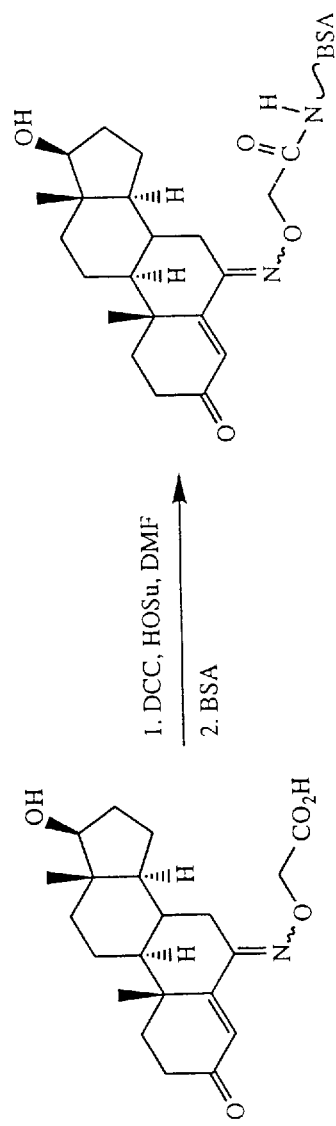
FIG. 4 illustrates the synthetic pathway for the preparation of an immunogen of the present invention by coupling 6-(O-carboxymethyl)-oxime testosterone to bovine serum albumin (BSA) according to the synthetic method of the present invention.

This example illustrates conjugation of 6-(O-carboxymethyl)-oxime testosterone to bovine serum albumin (FIG. 4).

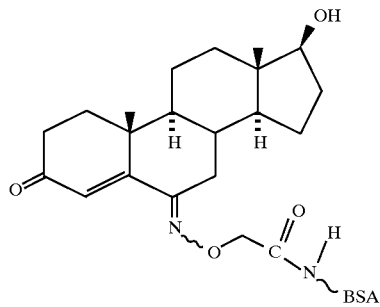

The reaction mixture of 6-(O-carboxymethyl)-oxime testosterone (50 mg, 0.133 mmol), DCC (27.5 mg, 0.133 mmol) and HOSu (18.4 mg, 0.160 mmol) in 0.8 mL of dry DMF was stirred at room temperature for 16 hours. Urea was filtered off through a disposable Pasteur pipette filled with cotton plug and washed with 0.8 mL of dry DMF. The combined filtrates were added dropwise to a solution of BSA (226 mg) in a mixture of phosphate buffer (4.0 mL, pH=7.80) and DMF (0.8 mL). The reaction mixture was stirred at room temperature for 16 hours, then transferred to a dialysis membrane tubing [SPECTRA/POR*2, 797925, Cat D1614-12, Size 25 mm, Dia 15.9 mm]. The tube was dialyzed with 4 L of a 0.1M phosphate buffer (pH=7.80) for 7 hours at room temperature, then against distilled water 4 L at: 7 hours, 17 hours, 7 hours, 17 hours, 7 hours, 17 hours. The immunogen was lyophilized and stored. TNBS titration showed 52% substitution of amino groups.

EXAMPLE 5

Figure 5:
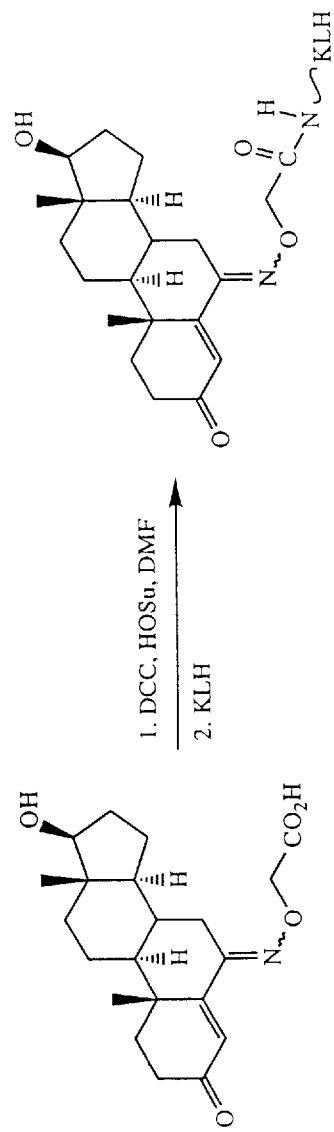
FIG. 5 illustrates the synthetic pathway for the preparation of an immunogen of the present invention by coupling 6-(O-carboxymethyl)-oxime testosterone to keyhole limpet hemocyanin (KLH) according to the synthetic method of the present invention.

This example illustrates conjugation of 6-(O-carboxymethyl)-oxime testosterone to keyhole limpet hemocyanin (FIG. 5).

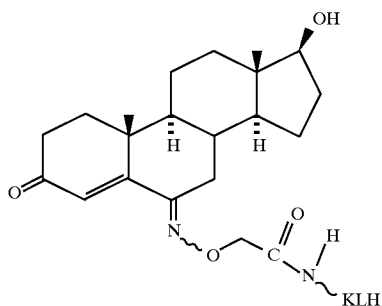

The reaction mixture of 6-(O-carboxymethyl)-oxime testosterone (50 mg, 0.133 mmol), DCC (27.5 mg, 0.133 mmol) and HOSu (18.4 mg, 0.160 mmol) in 0.8 mL of dry DMF was stirred at room temperature for 16 hours. Urea was filtered off through a disposable Pasteur pipette filled with cotton plug and washed with 0.8 mL of dry DMF. The combined filtrates were added dropwise to a solution of KLH (180 mg) in a mixture of phosphate buffer (8.0 mL, pH=7.80) and DMF (1.6 mL). The reaction mixture was stirred at room temperature for 16 hours, then transferred to a dialysis membrane tubing [SPECTRA/POR*2, 797925, Cat D1614-12, Size 25 mm, Dia 15.9 mm]. The tube was dialyzed with 4 L of a 0.1M phosphate buffer (pH=7.80) for 7 hours at room temperature, then against distilled water 4 L at: 7 hours, 17 hours, 7 hours, 17 hours, 7 hours, 17 hours. The immunogen was lyophilized and packed.

EXAMPLE 6

Figure 6:
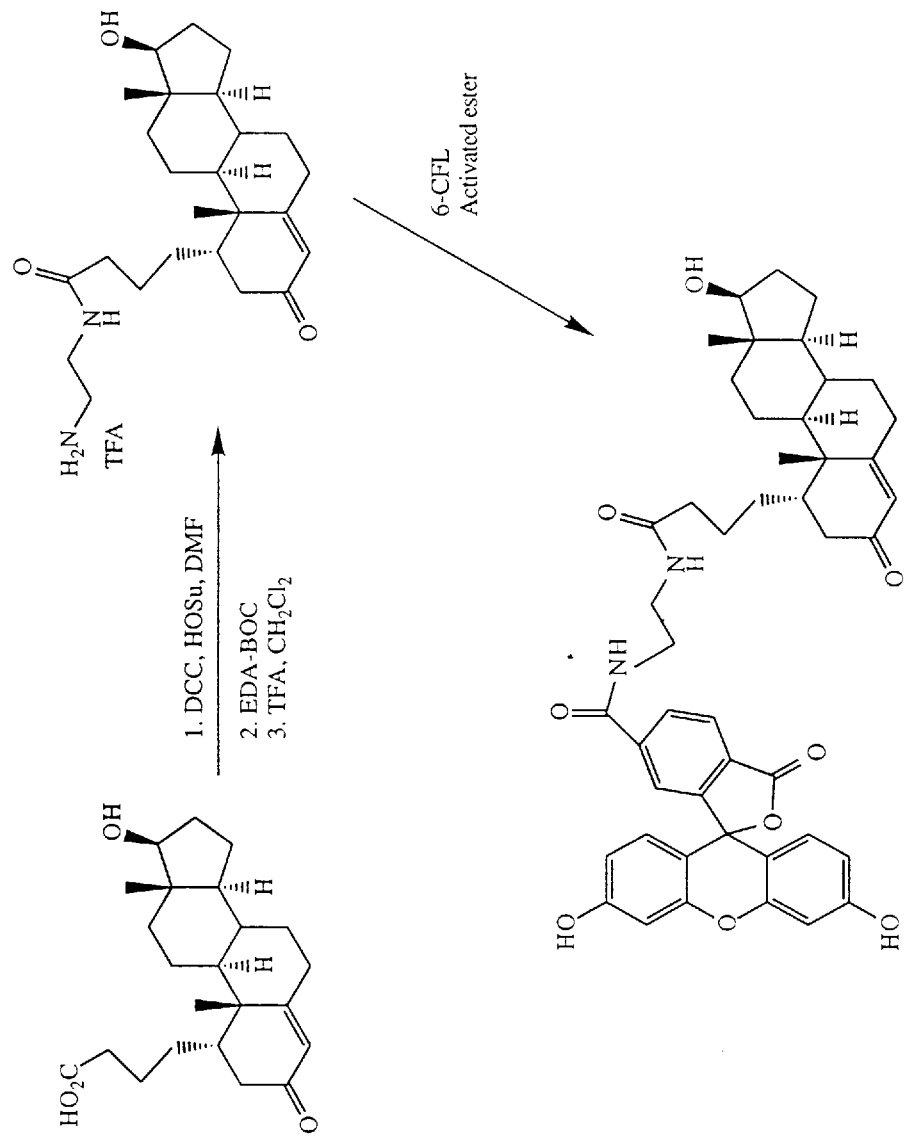
FIG. 6 illustrates the synthetic pathway for the preparation of a tracer of the present invention by coupling 1-α-(3'-carboxypropyl) testosterone to 6-carboxyfluorescein according to the synthetic method of the present invention.

This example and FIG. 6 illustrate the synthesis of the preferred Position 1 labeled reagent, a testosterone-fluorescein conjugate as represented in Formula 3:

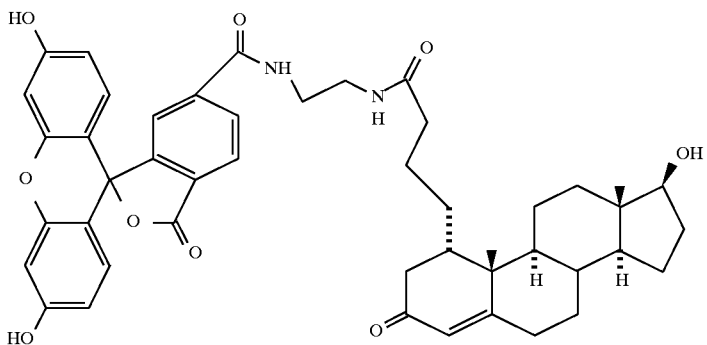

FORMULA 3

To the stirred solution of 1-α-(3'-carboxypropyl)-4-androsten-17β-ol-3-one, TBDMS-ether (95.4 mg, 0.254 mmol) and HOSu (58 mg, 0.504 mmol) in 2 mL of freshly degassed, dry DMF was added DCC (53 mg, 0.254 mmol) in one portion. The reaction mixture was stirred at room temperature for 16 hours and then N-BOC-Ethylenediamine (85 mg, 0.530 mmol) was added and the reaction mixture was stirred at room temperature for 16 hours. The solution was filtered through a disposable pipette plugged with cotton and applied to 2 preparatory TLC plates (2 mm thick, $C^{18}$ reversed phase plates). The plates were developed with a mixture of methanol/water/acetic acid (80/20/0.5, v/v). The desired bands were removed and extracted with 300 mnL of methanol. The methanol extract was filtered and evaporated under reduced pressure to give 77 mg (59%) of N-Boc protected ethylenediamide steroid. Mass spec. (DCI, $NH_3$) 517 $(M+H)^+$, 534 $(M+NH_4)^+$.

N-Boc ethylenediamide steroid (44 mg, 0.085 mmol) was dissolved in a mixture of 1/1 methylene chloride and trifluoroacetic acid (2 mL total) and stirred at room temperature for 10 minutes, reaction was complete by TLC. Solvents were removed under reduced pressure on a rotaevaporator. The deprotected amine was not separated and the residual material was used directly for the next coupling reaction.

6-Carboxyfluorescein (36 mg, 0.098 mmol), HOSu (21 mg, 0.182 mmol) and DCC in (20 mg, 0.097 mmol) 1 mL of dry, freshly degassed DMF were stirred at room temperature for 24 hours. Reaction was complete by TLC. This activated ester solution was added to 1-α-(3'-carboxypropyl) testosterone-EDA.TFA salt (0.098 mmol) and the whole mixture was diluted to 2 mL with dry DMF. Triethylamine (56 μL, 0.40 mmol) was added and the reaction mixture was stirred for 16 hours. The reaction mixture was filtered through a disposable pipette plugged with cotton and the filtrate was applied to a $C^{18}$ reversed phase preparatory TLC plate (1 mm thick). The plate was dried under vacuum and developed with methanol/water/acetic acid (70/30/0.5, v/v). The desired band was extracted with methanol (150 mL) and the methanol extract was evaporated under reduced pressure to afford 48 mg (63%) of tracer. Mass spec. (FAB) 775 $(M+H)^+$, 797 $(M+Na)^+$.

EXAMPLE 7

Figure 7:
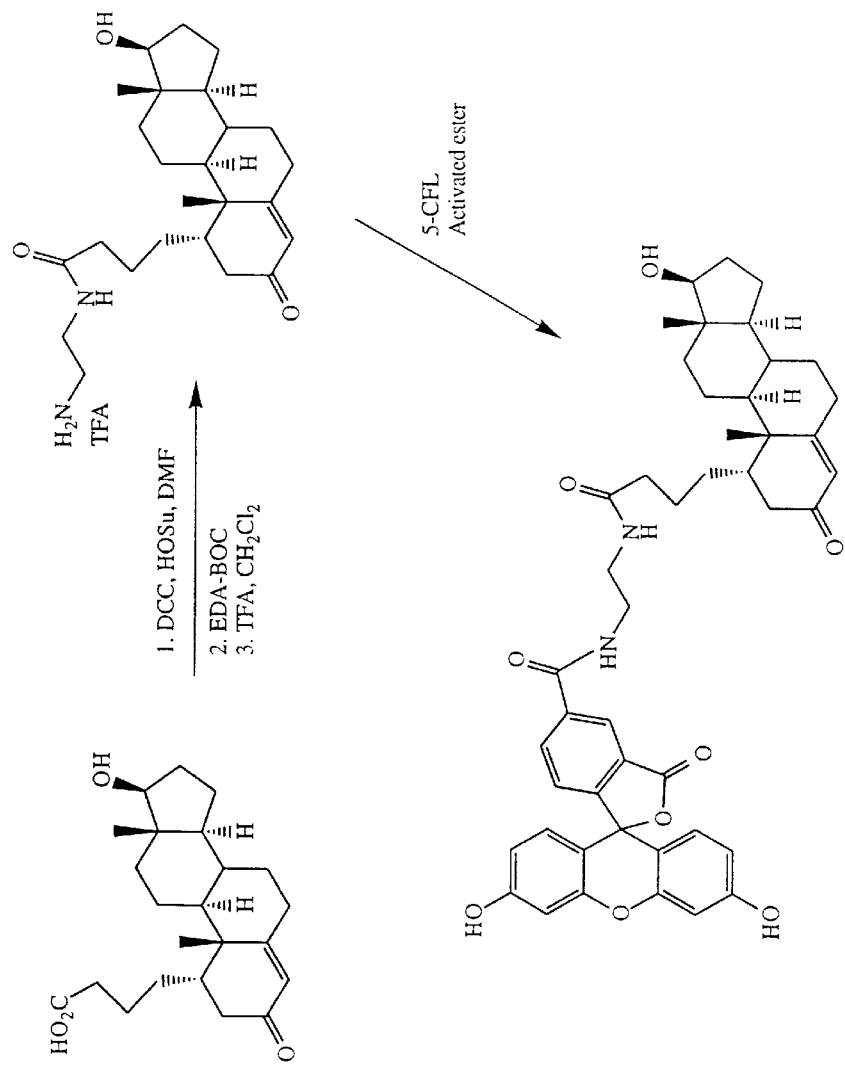
FIG. 7 illustrates the synthetic pathway for the preparation of a tracer of the present invention by coupling 1-α-(3'-carboxypropyl) testosterone to 5-carboxyfluorescein according to the synthetic method of the present invention.

This example and FIG. 7 illustrate the synthesis of another Position 1 labeled reagent, another testosterone-fluorescein conjugate which corresponds to the formula:

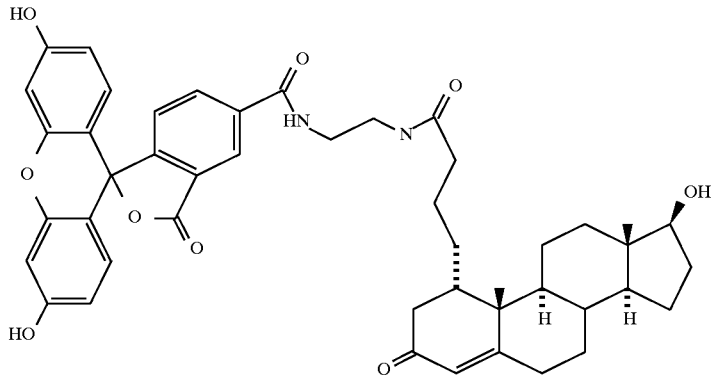

To the stirred solution of 1-α-(3'-carboxypropyl)-4-androsten-17β-ol-3-one, TBDMS-ether (95.4 mg, 0.254 mmol) and HOSu (58 mg, 0.504 mmol) in 2 mL of freshly degassed, dry DMF was added DCC (53 mg, 0.254 mmol) in one portion. The reaction mixture was stirred at room temperature for 16 hours and then N-BOC-Ethylenediamine (85 mg, 0.530 mmol) was added and the reaction mixture was stirred at room temperature for 16 hours. The solution was filtered through a disposable pipette plugged with cotton and applied to 2 preparatory TLC plates (2 mm thick, $C^{18}$ reversed phase plates). The plates were developed with a mixture of methanol/water/acetic acid (80/20/0.5, v/v). The desired bands were removed and extracted with 300 mL of methanol. The methanol extract was filtered and evaporated under reduced pressure to give 77 mg (59%) of N-Boc protected ethylenediamide steroid. Mass spec. (DCI, $NH_3$) 517 $(M+H)^+$, 534 $(M+NH_4)^+$.

N-Boc ethylenediamide steroid (44 mg, 0.085 mmol) was dissolved in a mixture of 1/1 methylene chloride and trifluoroacetic acid (2 mL total) and stirred at room temperature for 10 minutes, reaction was complete by TLC. Solvents were removed under reduced pressure on a rotaevaporator. The deprotected amine was not separated and the residual material was used directly for the next coupling reaction.

5-Carboxyfluorescein (20.3 mg, 0.054 mmol), HOSu (12 mg, 0.104 mmol) and DCC (11 mg, 0.054 mmol) in 0.5 mL of DMF were stirred at room temperature for 24 hours. Reaction was complete by TLC. This activated ester solution was added to 1-α-(3'-carboxypropyl) testosterone-EDA.TFA salt (0.072 mmol) and the whole mixture was diluted to 1 mL with dry DMF. Triethylamine (30 μL, 0.22 mmol) was added and the reaction mixture was stirred for 16 hours. The reaction mixture was filtered through a disposable pipette plugged with cotton and the filtrate was applied to a $C^{18}$ reversed phase preparatory TLC plate (1 mm thick). The plate was dried under vacuum and developed with methanol/water/acetic acid (70/30/0.5, v/v). The desired band was extracted with methanol (150 mL) and the methanol extract was evaporated under reduced pressure to afford 31 mg of (75%) tracer. Mass spec. (FAB) 775 (M+H)$^+$, 797 (M+Na)$^+$.

EXAMPLE 8

Figure 8:
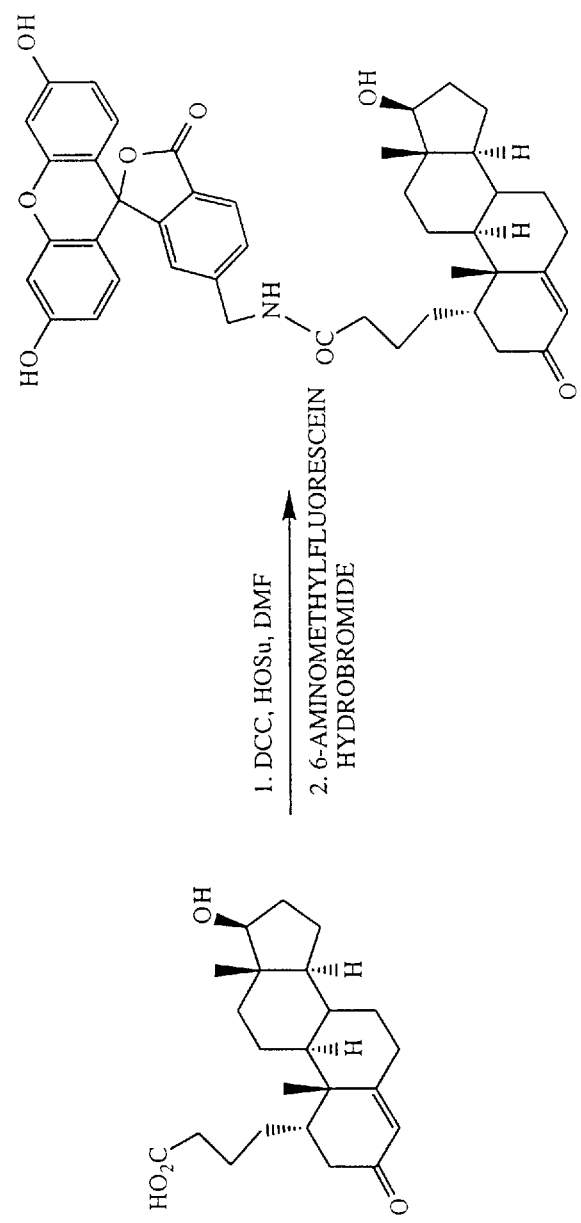
FIG. 8 illustrates the synthetic pathway for the preparation of a tracer of the present invention by coupling 1-α-(3'-carboxypropyl) testosterone to 6-aminomethylfluorescein according to the synthetic method of the present invention.

This example illustrates coupling of 1-α-(3'-carboxypropyl), testosterone to 6-aminomethylfluorescein (FIG. 8) to produce a tracer which corresponds to the formula:

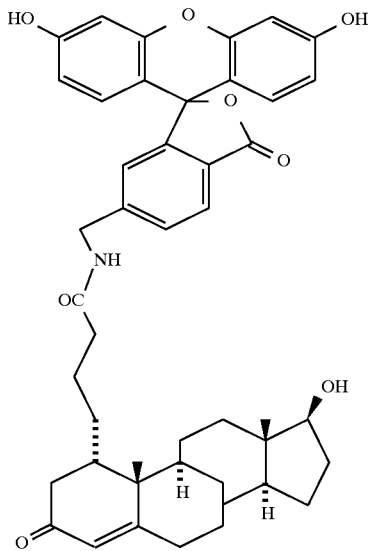

1-α-(3'-carboxypropyl) testosterone (55 mg, 0.147 mmol), HOSu (29 mg, 0.252 mmol) and DCC (26 mg, 0.126 mmol) in 0.5 mL of dry, freshly degassed DMF were stirred at room temperature for 16 hours after which 6-aminomethylfluorescein hydrobromide (56 mg, 0.126 mmol) and triethylamine (70 μL, 0.50 mmol) were added. The reaction mixture was stirred at room temperature for an additional 16 hours. Reaction was complete by TLC. The reaction mixture was applied to a 2 mm preparatory plate (regular phase), dried under vacuum and developed (methylene chloride/methanol/acetic acid, 92/8/0.5, v/v). Desired band was removed and extracted with 150 mL of 10% methanol in methylene chloride. Solvents were evaporated under reduced pressure on a rotaevaporator to afford 36 mg (34%) of tracer. Mass spec. (FAB) 718 (M+H)$^+$.

EXAMPLE 9

Figure 9:
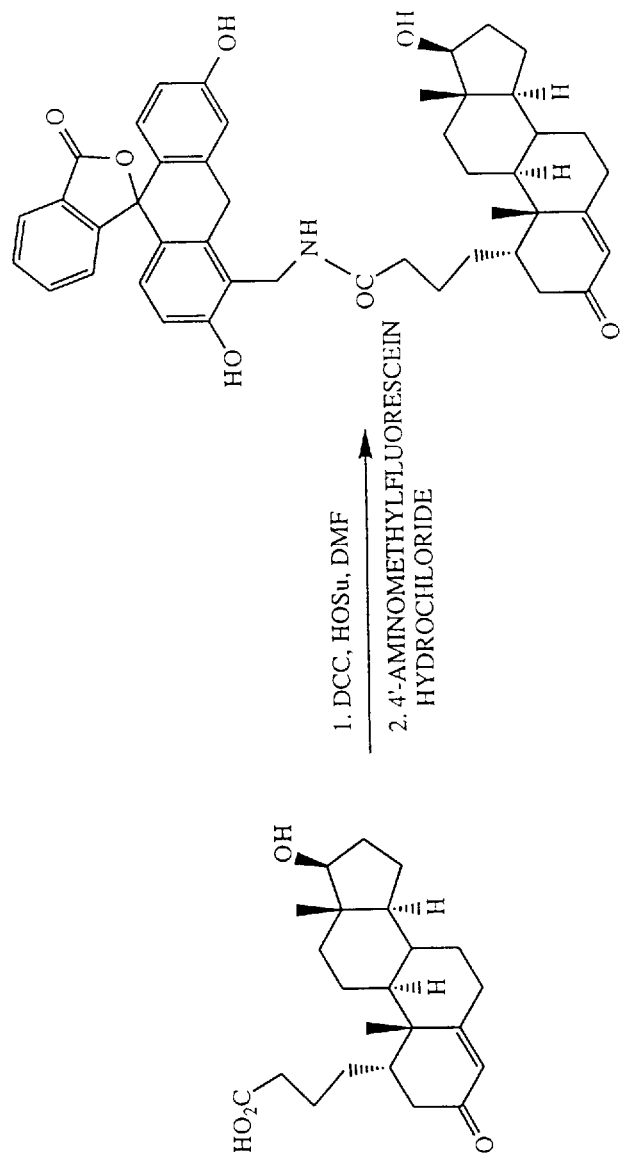
FIG. 9 illustrates the synthetic pathway for the preparation of a tracer of the present invention by coupling 1-α-(3'-carboxypropyl) testosterone to 4'-aminomethylfluorescein according to the synthetic method of the present invention.

This example illustrates coupling of 1-α-(3'-carboxypropyl) testosterone to 4'-aminomethylfluorescein (FIG. 9) to produce a tracer which corresponds to the following formula:

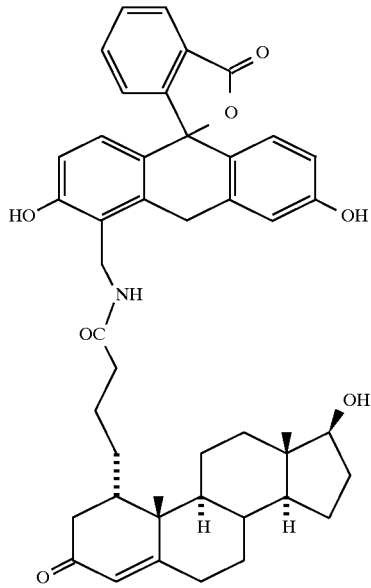

1-α-(3'-carboxypropyl) testosterone (55 mg, 0.147 mmol), HOSu (29 mg, 0.252 mmol) and DCC (26 mg, 0.126 mmol) in 0.5 mL of dry, freshly degassed DMF were stirred at room temperature for 16 hours after which 4'-aminomethylfluorescein hydrochloride (50 mg, 0.126 mmol) and triethylamine (35 μL, 0.25 mmol) were added. The reaction mixture was stirred at room temperature for 16 hours. Reaction was complete by TLC. The reaction mixture was applied to a 2 mm preparatory plate (regular phase), dried under vacuum and developed (methylene chloride/methanol/acetic acid, 92/8/0.5, v/v). Desired band was removed and extracted with 150 mL of 10% methanol in methylene chloride. Solvents were evaporated under reduced pressure on a rotaevaporator to afford 40 mg (38%) of tracer. Mass spec. (FAB) 718 (M+H)$^+$.

EXAMPLE 10

Figure 10:
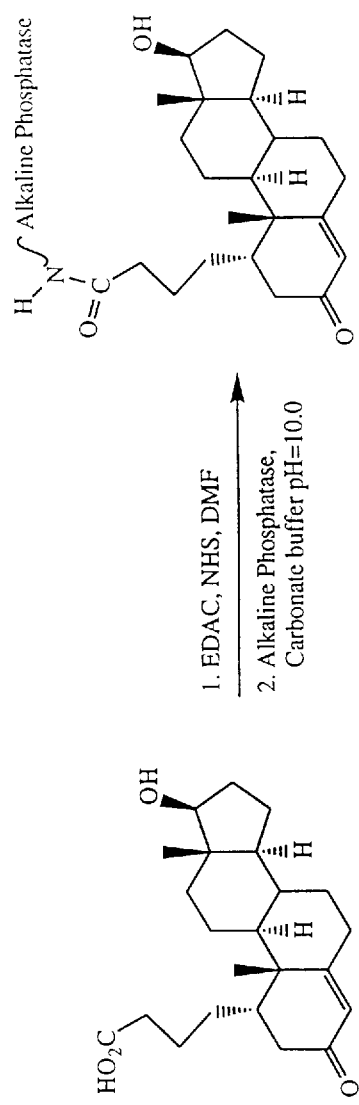
FIG. 10 illustrates the synthetic pathway for the preparation of a tracer of the present invention by coupling 1-α-

This example illustrates conjugation of 1-α-(3'-carboxypropyl) testosterone to alkaline phosphatase (FIG. 10).

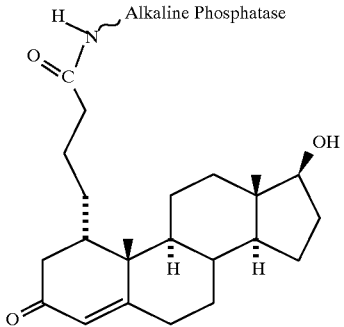

1-α-(3'-carboxypropyl) testosterone (3.1 mg, 0.0083 mmol), NHS (1.09 mg, 0.0095 mmol) and EDAC (1.6 mg, 0.0083 mmol) in 60.8 μl of freshly degassed, dry DMF were mixed for 1 hour at room temperature. 3.5 μl (7×10$^{-4}$ mmol) of the above reaction mixture was added to 496.5 μl of freshly degassed, dry DMF. To 300 μl (4.9×10$^{-6}$ mmol) of the reaction mixture was added alkaline phosphatase (2.9× $10^{-5}$ mmol), and pH 10.0 bicarbonate buffer (0.02 mmol, 1.7 mg sodium bicarbonate and 0.02 mmol, 2.1 mg sodium carbonate). The reaction was mixed for 16 hours at room temperature, followed by column chromatography, using G-25 sephadex, to result in the desired testosterone conjugate.

EXAMPLE 11

This example illustrates coupling of 6-(O-carboxymethyl)-oxime of testosterone to 4'-aminomethylfluorescein (FIG. 11) to produce a tracer which corresponds to the following formula:

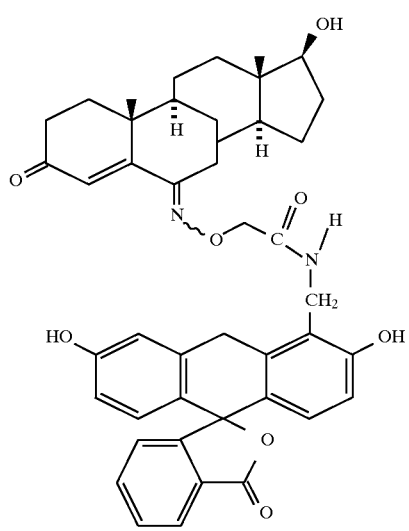

6-(O-carboxymethyl)-oxime testosterone of testosterone (19.2 mg, 0.051 mmol), HOSu (11.8 mg, 0.103 mmol) and DCC (19.5 mg, 0.095 mmol) in 0.5 mL of freshly degassed, dry DMF were stirred for 16 hours at room temperature. Activated ester was not isolated. To the reaction mixture was added 4'-aminomethylfluorescein hydrochloride (21 mg, 0.051 mmol) and triethylamine (28 μL, 0.20 mmol). After stirring at room temperature for 16 hours, the reaction mixture was applied to regular phase preparatory silica gel plate, dried under vacuum and developed (methylene chloride/methanol/acetic acid, 92/8/0.5, v/v). The desired band was removed and extracted with 50 mL of 10% methanol in methylene chloride. Mass spec. (FAB) 719 $(M+H)^+$.

EXAMPLE 12

This example illustrates conjugation of 6-(O-carboxymethyl)-oxime testosterone to alkaline phosphatase (FIG. 12).

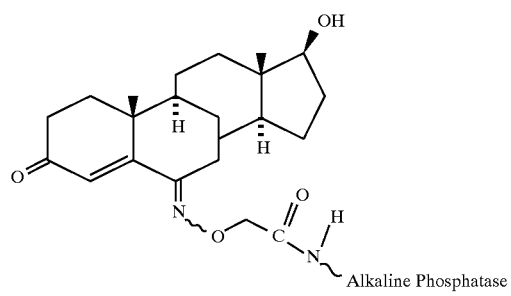

6-(O-carboxymethyl)-oxime testosterone 6-(O-carboxymethyl)-oxime testosterone (3.1 mg, 0.0083 mmol), NHS (1.09 mg, 0.0095 mmol) and EDAC (1.6 mg, 0.0083 mmol) in 60.8 μl of freshly degassed, dry DMF were mixed for 1 hour at room temperature. 3.5 μl ($7\times10^{-4}$ mmol) of the above reaction mixture was added to 496.5 μl of freshly degassed, dry DMF. To 300 μl ($4.9\times10^{-6}$ mmol) of the reaction mixture was added alkaline phosphatase (2.9× $10^{-5}$ mmol), and pH 10.0 bicarbonate buffer (0.02 mmol, 1.7 mg sodium bicarbonate and 0.02 mmol, 2.1 mg sodium carbonate). The reaction was mixed for 16 hours at room temperature, followed by column chromatography, using G-25 SEPHADEX, to result in the desired testosterone conjugate.

EXAMPLE 13

IMMUNIZATION STRATEGY

Four groups, each represented by six rabbits, were immunized with one of four different immunogens: (a) 6-(O-carboxymethyl)-oxime testosterone coupled to BSA {herein also referred to as 6-(O-carboxymethyl)-oxime testosterone:BSA, the formula of which is shown in Example 4}, (b) 6-(O-carboxymethyl)-oxime testosterone coupled to KLH {herein also referred to as 6-(O-carboxymethyl)-oxime testosterone:KLH; the formula of which is shown in Example 5}, (c) 1-α-(3'-carboxypropyl) testosterone coupled to BSA (Example 2), and (d) 1-α-(3'-carboxypropyl) testosterone coupled to KLH (Example 3). Initially, blood was obtained from each rabbit to use as a reference in evaluation of future bleeds. Rabbits were injected in the popliteal lymph node (PLN) with 0.5 mg of antigen emulsified in Freund's Complete Adjuvant. At three week intervals, the rabbits were boosted intramuscularly with 0.250 mg of antigen emulsified with Freund's Incomplete Adjuvant (FIA). Production bleeds (50 ml) were obtained 10 days after the initial injection and the subsequent boosts.

Antibody maturity was obtained after 3–4 months. Production bleeds at 25 ml/rabbit/month were collected for an additional 12 months from those rabbits showing acceptable specificity. Production bleeds were collected and pooled to form a representative pool of antisera.

SERA EVALUATION

The production bleeds were further evaluated on the IMx® instrument for specificity and the ability to construct a calibration curve using the labeled reagent outlined in Example 10, and the methods outlined in Examples 14, 16, 17, and 18.

EXAMPLE 14

PROTEIN A PURIFICATION OF ANTISERA

The general procedure for Protein A purification follows. Purification of antiserum at 232.5 mg by column chromatography [20 ml Protein A gel (Pierce, Cat #20366g), 1.5M glycine/3M sodium chloride pH 9.0 to 0.1M citric acid pH 3.0 as eluents] afforded 70 mg of purified material. The eluate was dialyzed against 10 mM phosphate, 100 mM sodium chloride, pH 7.2 (3.0 liters) for 16 hours at 2°–8° C. The material was then concentrated using a MILLIPORE IMMERSIBLE CX-30 Ultrafiltration Unit (Catalog #PTTK11K25) to a protein concentration of approximately 5 mg/ml using 10 mM phosphate, 100 mM sodium chloride, pH 7.2 (100 ml). The concentrated material was then filtered through a 0.2 um filter.

EXAMPLE 15

PREPARATION OF 6-(O-CARBOXYMETHYL)-OXIME TESTOSTERONE:AFFI-GEL 102 AFFINITY RESIN

The following example illustrates the preparation of an affinity resin that was used to further purify the antisera obtained from Example 14.

AFFI-GEL 102 gel (10.0 ml, Bio-Rad, Catalog #153-2401) was washed with 100.0 ml of 100% ethanol. 6-(O-carboxymethyl)-oxime testosterone (61.8 mg, 165 umoles) in 10.0 ml 100% ethanol was added to 10.0 ml of the washed Affi-Gel 102 resin. To this slurry was added EDAC (38.3 mg, 199.8 umoles) and NHS (19.98 mg, 199.8 umoles). The slurry was allowed to rotate gently for 4 hours. The resin was poured into a 20 ml glass column and washed with 100% ethanol (100 ml), water (100 ml) and 10 mM phosphate, 100 mM sodium chloride, pH 7.2 (100 ml). The column was then drained and stored for future use.

EXAMPLE 16

AFFINITY PURIFICATION OF ANTISERA DERIVED FROM IMMUNOGENS DESCRIBED IN EXAMPLES 4 AND USING THE 6-(O-CARBOXYMETHYL)-OXIME:AFFI-GEL 102 AFFINITY RESIN DESCRIBED IN EXAMPLE 15

Protein A purified antisera obtained from rabbits inoculated with either 6-(O-carboxymethyl)-oxime testosterone:BSA or 6-(O-carboxymethyl)-oxime testosterone:KLH were purified using the 6-(O-carboxymethyl) testosterone:Affi-gel 102 affinity resin of Example 15.

The general affinity purification procedure follows. The 6-(O-carboxymethyl)-oxime testosterone:AFFI-GEL 102 resin (10 ml, Example 15) was initially washed with 10 mM phosphate, 100 mM sodium chloride, pH 7.2 until the eluate was pH 7.2. Protein A purified antisera (50 mg, Example 14) was applied to the column and allowed to bind for 16 hours. The column was washed with 10 mM phosphate, 100 mM sodium chloride, pH 7.2 (100 ml), 2M sodium chloride (100 ml), and 10 mM phosphate, 100 mM sodium chloride, pH 7.2 (50 ml). Antibody was eluted with 0.1M citric acid pH 2.0 and afforded 5 mg of purified material.

The purified antisera were concentrated to approximately mg/ml with a MILLIPORE IMMERSIBLE CX-30 Ultrafiltration Unit (Catalog #PTTK11K25) and 10 mM phosphate, 100 mM sodium chloride, pH 7.2 (100 ml).

EXAMPLE 17

This example illustrates the method for covalently coupling antisera purified in Example 16 to carboxylate modified latex (CML) particles.

CLEANING LATEX PARTICLES

Most uniform latex particles are made by emulsion polymerization using surfactants. The surfactants (usually negatively charged) must be removed before the particles can be coated with protein. There are several methods of cleaning particles which are known to those skilled in the art. Particle clean-up methods as described by Seradyn (Microparticle Immunoassay Techniques, 1988) were followed with slight modification.

To 0.2 g latex particles (Seradyn, Carboxylate Modified Latex, 0.396 um diameter, MFG Lot #2179, PKG Lot #2B66) in 2 ml water was added 1 g of Bio-Rad mixed bed resin (Cat. #1427425). The slurry was mixed for 1 hour at room temperature. The reaction mixture was filtered on a glass-fritted filter and the filtrate containing surfactant-free latex particles was diluted with water/0.1% sodium azide to give a 3.2% latex particle solution.

COVALENT COUPLING OF ANTIBODY (EXAMPLE 16) TO CLEANED CARBOXYLATE MODIFIED LATEX PARTICLES

To 3 mg of latex particles as described above was added MES buffer pH 4.5 (0.025 mmol). After mixing at room temperature for 1 minute, 0.1 mg of affinity purified antibody (Example 16) was added. After mixing for an additional minute, $2.09 \times 10^{-3}$ mmol of EDAC was added and the reaction mixture was mixed for 1 hour at room temperature. The particles were purified by centrifugation, washing the pellet twice with 0.1% Tween 20 and once with IMx® MEIA Line Diluent. The particles were then resuspended in latex particle storage diluent (0.05 mmoles Tris, 0.1 mmoles sodium chloride, 0.136 g sucrose, 125 μg rabbit IgG at pH 7.4).

EXAMPLE 18

MICROPARTICLE ENZYME IMMUNOASSAY FOR TESTOSTERONE

The affinity purified antisera coupled to latex particles (Example 17) and the 1-α-(3'-carboxypropyl) testosterone alkaline phosphatase tracer (Example 10) were used in the commercially available IMx® instrument. General operation of the IMx® instrument was according to the vendor's recommended protocol in the IMx® System Operation Manual. The IMx® System Operation Manuals contain: 1) theory of operation: microparticle enzyme immunoassay; 2) operational precautions and limitations; 3) daily start-up procedure; 4) monthly and periodic procedures necessary for quality control to be maintained. A calibration curve and crossreactivity studies were conducted using the following IMx® Assay protocol.

The IMx® Testosterone assay is based on the Microparticle Enzyme Immunoassay (MEIA) technology. The IMx® Testosterone reagents and sample were added to the reaction cell in the following manner: 1) latex particles coupled to antibody ($2.5 \times 10^{-6}$ g of latex-antibody conjugate in latex particle storage diluent; Example 17), glycine ($3.9 \times 10$-5 moles), and 50 μl of specimen were added to 115 μl of IMx® MEIA Line Diluent at a final pH of 5.5 in the incubation well of the reaction cell by the probe/electrode assembly; 2) After incubation for 514 seconds, 175 μl/250 μl of the incubation mixture is transferred to the glass fiber matrix of the reaction cell and washed twice with IMx® MEIA Line Diluent; 3) Labeled reagent ($2.1 \times 10^{-9}$ moles of protein, Example 10) was then added to the glass fiber matrix of the reaction cell; 4) After a six second incubation, unbound labeled reagent was removed by three washes with IMx® MEIA Line Diluent; 5) Antibody substrate (4-Methylumbelliferyl Phosphate) was then added to the glass fiber matrix of the reaction cell and the fluorescent product is measured by the MEIA optical assembly of the IMx® instrument.

Affinity purified antisera that were coupled to latex particles (Example 17) were evaluated for their ability to bind testosterone, the 1-α-(3'-carboxypropyl) testosterone:alkaline phosphatase labeled reagent (Example 10) and the 6-(O-carboxymethyl)-oxime testosterone:alkaline phosphatase labeled reagent (Example 12). As shown in FIG. 13, a standard curve was obtained using the MEIA assay for testosterone. A superior standard was obtained using the 1-α-(3'-carboxypropyl) testosterone:alkaline phosphatase labeled reagent (Example 10).

The cross-reactivity of the affinity purified antisera which were coupled to latex particles (Example 17) was evaluated in the MEIA assay. Compounds which are structurally related to testosterone and are present in male or female blood from an endogenous or exogenous origin were tested (Table 1).

TABLE 1

| Compound | % Cross-reactivity |
| --- | --- |
| 5α-dihydrotestosterone | 8.88 |
| Androstenedione | 0.8 |
| Danazol | 0.00 |
| DHEA-s | 0.00 |
| DHEA | 0.00 |
| Progesterone | 0.00 |
| 11-Deoxycortisol | 0.00 |
| Estradiol | 0.00 |
| 17α-hydroxyprogesterone caproate | ≦0.14 |
| Medroxyprogesterone acetate | ≦0.14 |
| Norethisterone | ≦0.14 |
| Norgestrel | ≦0.14 |
| Ethinylestradiol | ≦0.14 |

TABLE 1 illustrates cross-reactivities of compounds which may interfere with the described Assay using the affinity purified antisera coupled to latex particles (of Example 17) and the 1-α-(3'-carboxypropyl) testosterone:alkaline phosphatase labeled reagent (of Example 10). The compounds in Table 1 are typically used in commercial assays to determine the specificity of a testosterone assay. The low cross-reactivities show that the assay, in particular the antibodies, is highly specific for testosterone.

We claim:

1. A competitive immunoassay method for the quantification of testosterone in a test sample, said method comprising the steps of:

(a) contacting said test sample with a Position 1 labeled reagent, and antibodies which are capable of binding said Position 1 labeled reagent and said analyte, to form a reaction solution, the Position 1 labeled reagent having the following formula:

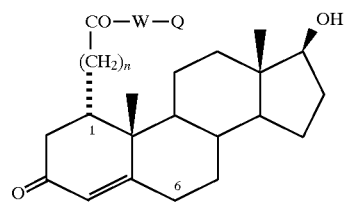

wherein

Q is a detectable moiety, W is a linking moiety, and n is between 2 and 10, inclusively; and (b) measuring the amount of said Position 1 labeled reagent in said reaction solution which is bound to said antibodies as a function of the amount of testosterone in said test sample.

2. The method of claim 1, wherein W consists of from 0 to 50 carbon and heteroatoms, including not more than ten heteroatoms, arranged in a straight or branched chain or cyclic moiety or any combination thereof, saturated or unsaturated, with the provisos that: (1) not more than two heteroatoms may be directly linked, (2) W cannot contain —O—O— linkages, (3) the cyclic moieties contain 6 or fewer members, and (4) branching may occur only on carbon atoms.

3. The method of claim 2, wherein the heteroatoms are selected from the group consisting of: nitrogen, oxygen, and sulfur.

4. The method of claim 1, wherein said detectable moiety is selected from the group consisting of enzymes, fluorescent molecules, and chemiluminescent molecules.

5. The method of claim 1, wherein the Position 1 labeled reagent has a formula selected from the group consisting of the Examples 6 to 10 below.

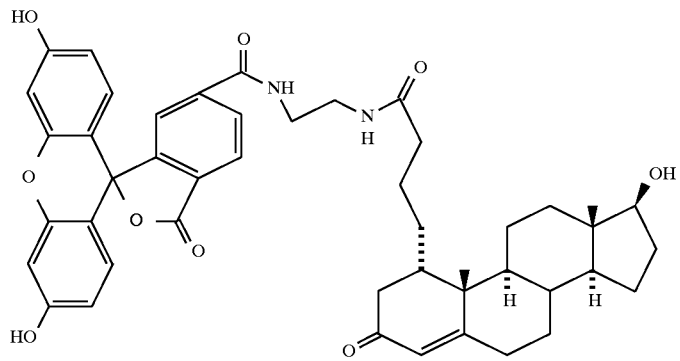

Example 6

-continued
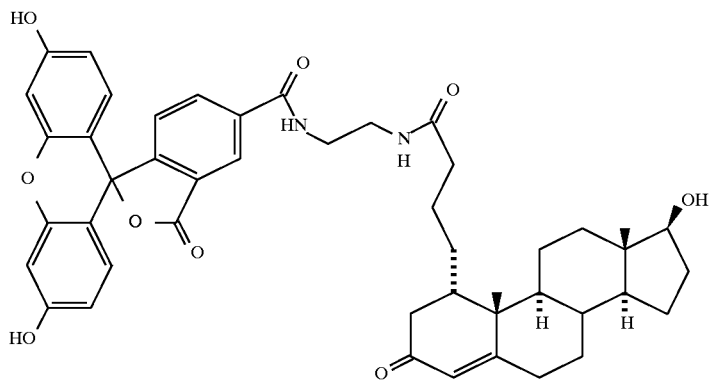
Example 7
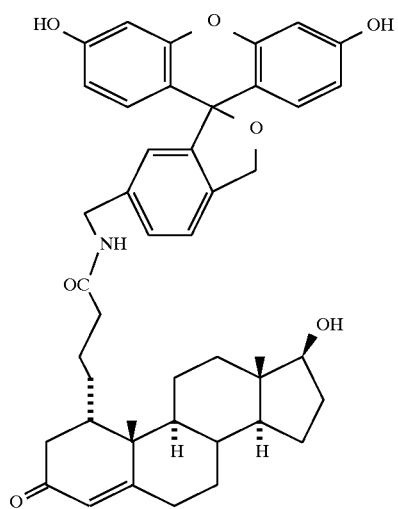
Example 8
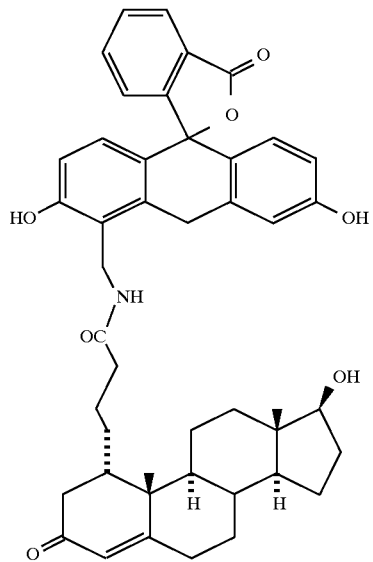
Example 9

-continued

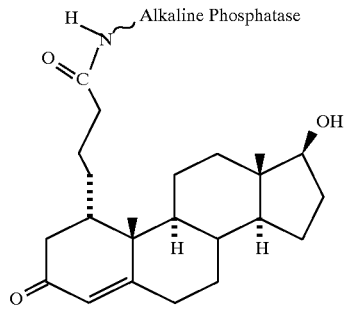

6. The method of claim 1, wherein said antibodies are produced with an immunogen with the structural formula selected from the group consisting of Formula 5 and Formula 6 shown below:

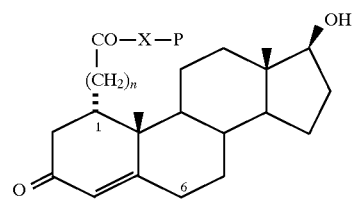

Formula 5

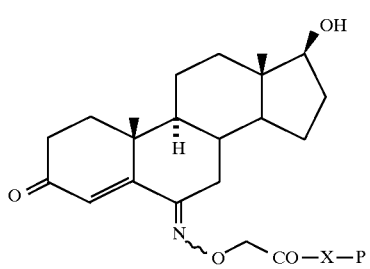

Formula 6 wherein:
(a) P is an immunogenic carrier material, and X is a second linking moiety,
(b) n is between 1 to 10 inclusively, and
(c) the degree of substitution of P by the testosterone derivative is between 1% to 100%, inclusively.

7. The method of claim 6, wherein X consists of from 0 to 50 carbons and heteroatoms, including not more than ten heteroatoms, arranged in a straight or branched chain or cyclic moiety or any combination thereof, saturated or unsaturated, with the provisos that: (1) not more than two heteroatoms may be directly linked, (2) X cannot contain —O—O— linkages, (3) the cyclic moieties contain 6 or fewer members, and (4) branching may occur only on carbon atoms.

8. The method of claim 7, wherein W consists of from 0 to 50 carbons and heteroatoms, including not more than ten heteroatoms, arranged in a straight or branched chain or cyclic moiety or any combination thereof, saturated or unsaturated, with the provisos that: (1) not more than two heteroatoms may be directly linked, (2) W cannot contain —O—O— linkages, (3) the cyclic moieties contain 6 or fewer members, (4) branching may occur only on carbon atoms, and (5) X can be the same or different from W.

9. The method of claim 6, wherein W consists of from 0 to 50 carbons and heteroatoms, including not more than ten heteroatoms, arranged in a straight or branched chain or cyclic moiety or any combination thereof, saturated or unsaturated, with the provisos that: (1) not more than two heteroatoms may be directly linked, (2) W cannot contain —O—O— linkages, (3) the cyclic moieties contain 6 or fewer members, and (4) branching may occur only on carbon atoms.

10. The method of claim 6, wherein the immunogenic carrier is selected from the group consisting of: proteins, polypeptides, peptides, carbohydrates, polysaccharides, lipopolysaccharides, poly(amino)acids, and nucleic acids.

11. The method of claim 10, wherein said immunogenic carrier material is selected from the group consisting of bovine serum albumin, keyhole limpet hemocyanin, and thyroglobulin.

12. The method of claim 11, wherein the immunogen is of the formula selected from the group consisting of Examples 2 to 5 below.

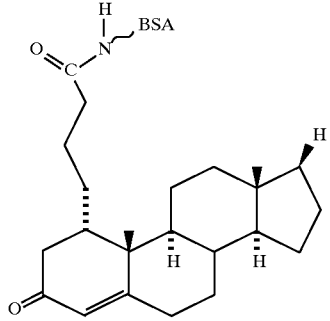

Example 2

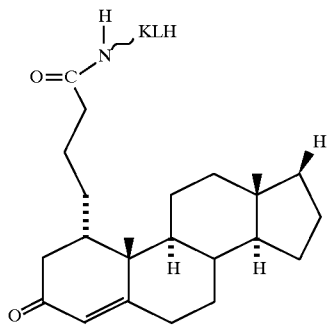

Example 3

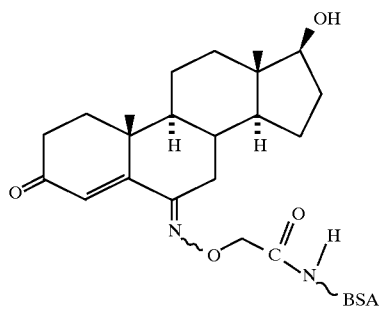

Example 4

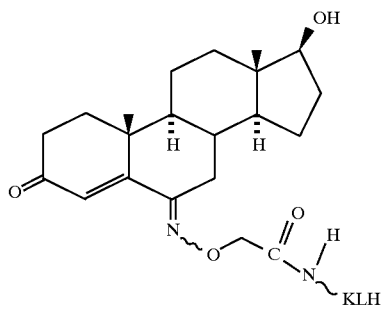

Example 5

13. The method of claim 6, wherein the immunogen is of Formula 6.

14. The method of claim 13, wherein X consists of from 0 to 50 carbons and heteroatoms, including not more than ten heteroatoms, arranged in a straight or branched chain or cyclic moiety or any combination thereof, saturated or unsaturated, with the provisos that: (1) not more than two heteroatoms may be directly linked, (2) X cannot contain —O—O— linkages, (3) the cyclic moieties contain 6 or fewer members, and (4) branching may occur only on carbon atoms.

15. The method of claim 13, wherein W consists of from 0 to 50 carbons and heteroatoms, including not more than ten heteroatoms, arranged in a straight or branched chain or cyclic moiety or any combination thereof, saturated or unsaturated, with the provisos that: (1) not more than two heteroatoms may be directly linked, (2) W cannot contain —O—O— linkages, (3) the cyclic moieties contain 6 or fewer members, and (4) branching may occur only on carbon atoms.

16. The method of claim 15, wherein W consists of from 0 to 50 carbons and heteroatoms, including not more than ten heteroatoms, arranged in a straight or branched chain or cyclic moiety or any combination thereof, saturated or unsaturated, with the provisos that: (1) not more than two heteroatoms may be directly linked, (2) W cannot contain —O—O— linkages, (3) the cyclic moieties contain 6 or fewer members, (4) branching may occur only on carbon atoms, and (5) X can be the same or different from W.

17. The method of claim 16, wherein the heteroatoms are selected from the group consisting of: nitrogen, oxygen, and sulfur.

18. The method of claim 17, wherein W and X are selected from the group consisting of: alkylene, arylalkylene and alkylene substituted cycloalkylene groups.

19. The method of claim 16, wherein said labeled reagent is of the formula selected from the group of labeled reagents having formulae represented by Examples 6 to 10 below.

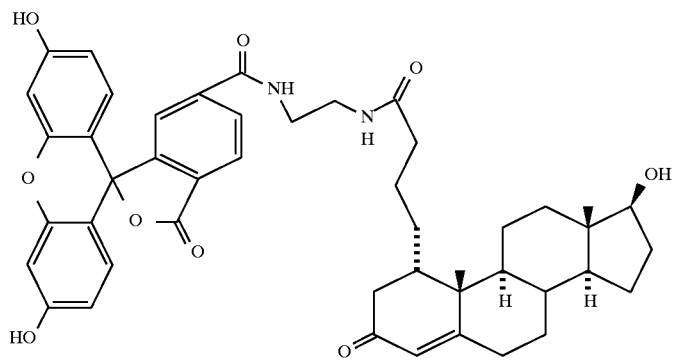

Example 6

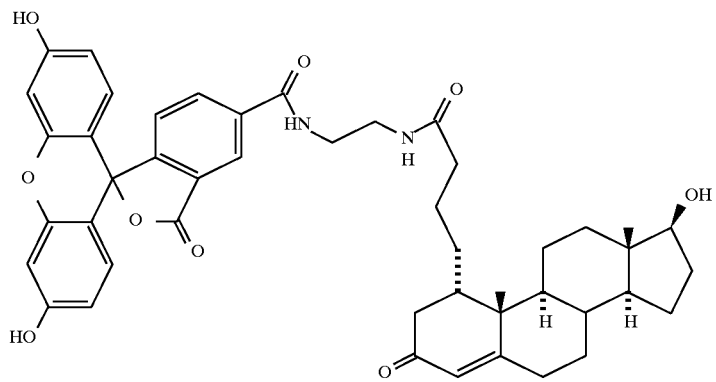

Example 7

Example 8
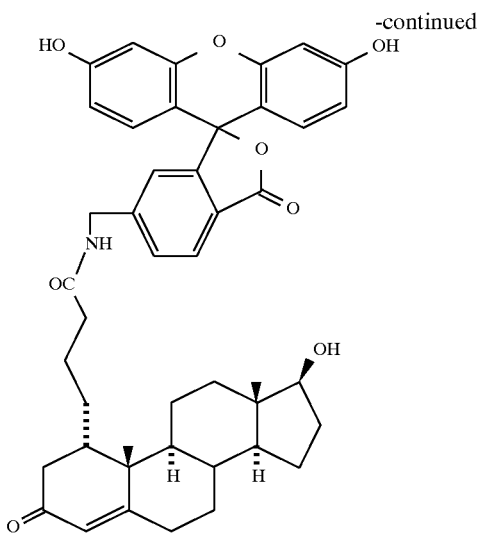
Example 9
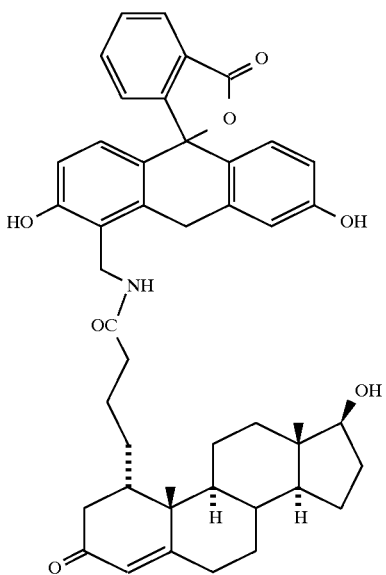
Example 10
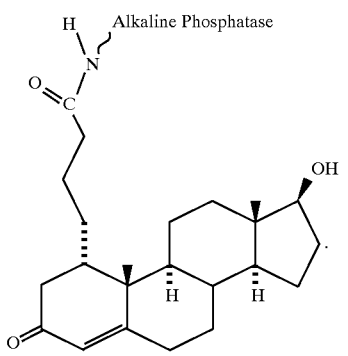
20. The method of claim 6, wherein the labeled reagent is of the formula of Example 10.
21. The method of claim 20, wherein said immunogen has the formula selected from the group consisting of Examples 4 and 5.
* * * * *

UNITED STATES PATENT AND TRADEMARK OFFICE
CERTIFICATE OF CORRECTION

PATENT NO. : 5,851,781  
DATED : December 22, 1998  
INVENTOR(S) : Adamczyk et al.

Page 1 of 4

It is certified that error appears in the above-identified patent and that said Letters Patent is hereby corrected as shown below:

Column 33, Example 8, change

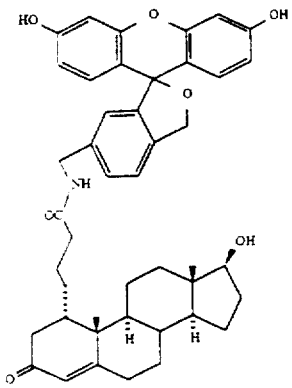

to

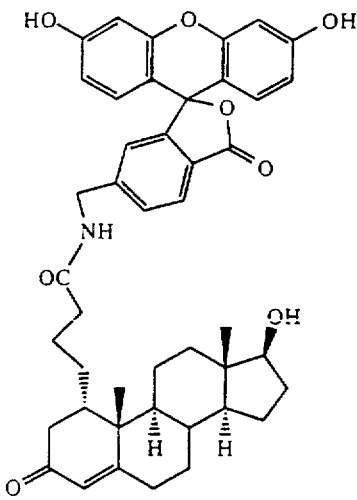

UNITED STATES PATENT AND TRADEMARK OFFICE
CERTIFICATE OF CORRECTION

PATENT NO. : 5,851,781  Page 2 of 4
DATED : December 22, 1998
INVENTOR(S) : Adamczyk et al.

It is certified that error appears in the above-identified patent and that said Letters Patent is hereby corrected as shown below:

Column 36, Example 2, change

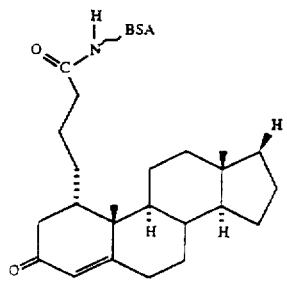

to

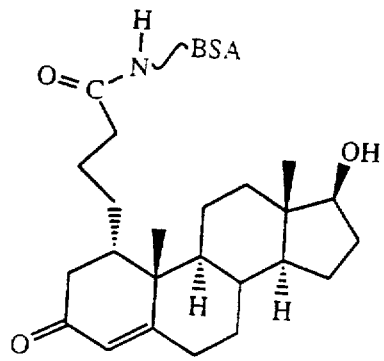

UNITED STATES PATENT AND TRADEMARK OFFICE
CERTIFICATE OF CORRECTION

PATENT NO. : 5,851,781                              Page 3 of 4
DATED : December 22, 1998
INVENTOR(S) : Adamczyk et al.

It is certified that error appears in the above-identified patent and that said Letters Patent is hereby corrected as shown below:

Column 36, Example 3, change

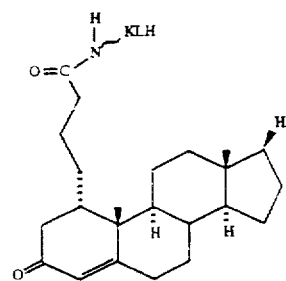

UNITED STATES PATENT AND TRADEMARK OFFICE
CERTIFICATE OF CORRECTION

PATENT NO. : 5,851,781
DATED : December 22, 1998
INVENTOR(S) : Adamczyk et al.

It is certified that error appears in the above-identified patent and that said Letters Patent is hereby corrected as shown below:

to

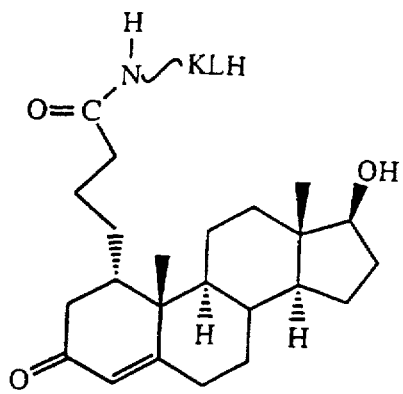

Signed and Sealed this

Sixth Day of July, 1999

Attest:

Q. TODD DICKINSON

Attesting Officer

Acting Commissioner of Patents and Trademarks